(12) United States Patent
Rabiner et al.

(10) Patent No.: US 9,427,289 B2
(45) Date of Patent: Aug. 30, 2016

(54) LIGHT SOURCE

(75) Inventors: Robert A. Rabiner, Tiverton, RI (US);
Dennis P. Colleran, North Attleboro, MA (US); Anthony W. O'Leary, Walpole, MA (US); Justin G. Dye, Mansfield, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 954 days.

(21) Appl. No.: 12/262,370

(22) Filed: Oct. 31, 2008

(65) Prior Publication Data

US 2009/0112196 A1 Apr. 30, 2009

Related U.S. Application Data

(60) Provisional application No. 60/984,241, filed on Oct. 31, 2007.

(51) Int. Cl.
*A61B 18/18* (2006.01)
*A61B 17/00* (2006.01)

(52) U.S. Cl.
CPC ...... *A61B 90/30* (2016.02); *A61B 2017/00734* (2013.01); *A61B 2090/306* (2016.02)

(58) Field of Classification Search
CPC .................. A61B 19/5202; A61B 2019/5206; A61B 17/8836; A61B 2017/564; A61B 2017/00734
USPC .......................... 606/2–19, 94–95; 607/88–94
See application file for complete search history.

(56) References Cited

U.S. PATENT DOCUMENTS

| | | |
|---|---|---|
| 3,485,520 A | 12/1969 | Alexander |
| 4,271,839 A | 6/1981 | Fogarty et al. |
| 4,280,233 A | 7/1981 | Raab ............................. 3/1.91 |
| 4,294,251 A | 10/1981 | Greenwald et al. .......... 128/276 |
| 4,313,434 A | 2/1982 | Segal ............................. 128/92 |
| 4,341,691 A | 7/1982 | Anuta .......................... 523/116 |
| 4,369,772 A | 1/1983 | Miller |
| 4,414,608 A | 11/1983 | Furihata |
| 4,422,719 A | 12/1983 | Orcutt |
| 4,433,898 A | 2/1984 | Nasiri |
| 4,462,394 A | 7/1984 | Jacobs |
| 4,466,435 A | 8/1984 | Murray |

(Continued)

FOREIGN PATENT DOCUMENTS

| | | |
|---|---|---|
| DE | 40 28 466 | 3/1992 |
| EP | 0 709 698 | 5/1996 |

(Continued)

OTHER PUBLICATIONS

International Search Report based on PCT/US10/30275 dated Aug. 11, 2010.

(Continued)

*Primary Examiner* — Gary Jackson
*Assistant Examiner* — Scott T Luan
(74) *Attorney, Agent, or Firm* — Greenberg Traurig, LLP; David J. Dykeman; Roman Fayerberg

(57) ABSTRACT

Disposable light sources are disclosed herein. A device for connecting a fiber to a light source includes a light source, light director to focus light from the light source, the light director surrounding at least a portion of the light source, a power source providing energy to the light source, and a connector communicating light from the light source to a catheter.

26 Claims, 6 Drawing Sheets

(56) References Cited

U.S. PATENT DOCUMENTS

| | | | | |
|---|---|---|---|---|
| 4,562,598 | A | 1/1986 | Kranz | |
| 4,686,973 | A | 8/1987 | Frisch | 128/92 |
| 4,697,584 | A | 10/1987 | Haynes | 128/92 |
| 4,735,625 | A | 4/1988 | Davidson | 623/16 |
| 4,870,953 | A | 10/1989 | DonMicheal et al. | 604/22 |
| 4,888,024 | A | 12/1989 | Powlan | 623/23 |
| 4,892,550 | A | 1/1990 | Huebsch | |
| 4,904,391 | A | 2/1990 | Freeman | 210/695 |
| 4,961,424 | A | 10/1990 | Kubota et al. | 128/24 A |
| 4,963,151 | A | 10/1990 | Ducheyne et al. | 623/16 |
| 4,969,888 | A | 11/1990 | Scholten et al. | 606/94 |
| 5,030,093 | A | 7/1991 | Mitnick | 433/164 |
| 5,049,157 | A | 9/1991 | Mittelmeier et al. | 623/16 |
| 5,085,660 | A | 2/1992 | Lin | |
| 5,092,899 | A | 3/1992 | Forte | 623/23 |
| 5,102,413 | A | 4/1992 | Poddar | 606/62 |
| 5,108,404 | A | 4/1992 | Scholten et al. | 606/94 |
| 5,112,333 | A | 5/1992 | Fixel | |
| 5,207,669 | A * | 5/1993 | Baker et al. | 606/7 |
| 5,222,958 | A | 6/1993 | Chin | |
| 5,295,733 | A | 3/1994 | LeBegue | |
| 5,295,962 | A | 3/1994 | Crocker et al. | |
| 5,303,718 | A | 4/1994 | Krajicek | |
| 5,316,550 | A | 5/1994 | Forte | 623/23 |
| 5,336,699 | A | 8/1994 | Cooke et al. | 523/115 |
| 5,372,598 | A | 12/1994 | Luhr et al. | 606/69 |
| 5,376,123 | A | 12/1994 | Klaue et al. | |
| 5,391,144 | A | 2/1995 | Sakurai et al. | 604/22 |
| 5,415,654 | A | 5/1995 | Daikuzono | |
| 5,423,850 | A | 6/1995 | Berger | 606/192 |
| 5,432,876 | A | 7/1995 | Appeldorn et al. | |
| 5,443,468 | A | 8/1995 | Johnson | 606/80 |
| 5,462,552 | A | 10/1995 | Kiester | 606/92 |
| 5,480,400 | A | 1/1996 | Berger | 606/60 |
| 5,538,514 | A | 7/1996 | Hawkins | |
| 5,548,676 | A | 8/1996 | Savage, Jr. | |
| 5,554,111 | A | 9/1996 | Morrey et al. | 604/26 |
| 5,556,429 | A | 9/1996 | Felt | 623/16 |
| 5,571,204 | A | 11/1996 | Nies | |
| 5,658,310 | A | 8/1997 | Berger | 606/192 |
| 5,658,963 | A | 8/1997 | Qian et al. | |
| 5,705,181 | A | 1/1998 | Cooper et al. | 424/426 |
| 5,707,374 | A | 1/1998 | Schmidt | 606/85 |
| 5,713,901 | A | 2/1998 | Tock | |
| 5,795,353 | A | 8/1998 | Felt | 623/18 |
| 5,824,087 | A | 10/1998 | Aspden et al. | 623/16 |
| 5,827,289 | A | 10/1998 | Reiley et al. | 606/86 |
| 5,888,220 | A | 3/1999 | Felt et al. | 623/17 |
| 5,897,557 | A | 4/1999 | Chin et al. | 606/71 |
| 5,908,433 | A | 6/1999 | Eager et al. | 606/170 |
| 5,972,015 | A | 10/1999 | Scribner et al. | |
| 5,980,075 | A | 11/1999 | Sheaffer | |
| 5,980,253 | A | 11/1999 | Oxman et al. | |
| 5,987,199 | A | 11/1999 | Zarian et al. | |
| 5,989,230 | A | 11/1999 | Frassica | |
| 5,997,570 | A | 12/1999 | Ligtenberg et al. | |
| 6,008,264 | A | 12/1999 | Ostler | |
| 6,019,761 | A | 2/2000 | Gustilo | 606/62 |
| 6,019,774 | A | 2/2000 | Weiss et al. | 606/167 |
| 6,033,411 | A | 3/2000 | Preissman | 606/99 |
| 6,039,762 | A | 3/2000 | McKay | 623/17 |
| 6,042,380 | A | 3/2000 | De Rowe | 433/173 |
| 6,048,346 | A | 4/2000 | Reiley et al. | |
| 6,053,917 | A | 4/2000 | Sherman et al. | |
| 6,059,789 | A | 5/2000 | Dinger et al. | 606/96 |
| 6,066,154 | A | 5/2000 | Reiley et al. | 606/192 |
| 6,077,265 | A | 6/2000 | Werding et al. | |
| 6,079,868 | A | 6/2000 | Rydell | 366/189 |
| 6,103,203 | A | 8/2000 | Fischer | |
| 6,110,176 | A | 8/2000 | Shapira | 606/80 |
| 6,121,341 | A | 9/2000 | Sawhney et al. | 522/84 |
| 6,127,597 | A | 10/2000 | Beyar et al. | 623/16 |
| 6,136,011 | A | 10/2000 | Stambaugh | |
| 6,140,452 | A | 10/2000 | Felt et al. | 528/60 |
| 6,159,236 | A | 12/2000 | Biel | |
| 6,179,852 | B1 | 1/2001 | Strickland et al. | 606/167 |
| 6,195,477 | B1 | 2/2001 | Denuto et al. | |
| 6,200,134 | B1 | 3/2001 | Kovac et al. | 433/29 |
| 6,217,581 | B1 | 4/2001 | Tolson | 606/86 |
| 6,223,085 | B1 | 4/2001 | Dann et al. | |
| 6,224,630 | B1 | 5/2001 | Bao et al. | 623/17 |
| 6,235,043 | B1 | 5/2001 | Reiley et al. | |
| 6,241,734 | B1 | 6/2001 | Scribner et al. | 606/93 |
| 6,248,110 | B1 | 6/2001 | Reiley et al. | 606/93 |
| 6,248,131 | B1 | 6/2001 | Felt et al. | 623/17.12 |
| 6,254,571 | B1 | 7/2001 | Hart | |
| 6,258,089 | B1 | 7/2001 | Campbell et al. | |
| 6,261,289 | B1 | 7/2001 | Levy | |
| 6,280,456 | B1 | 8/2001 | Scribner et al. | |
| 6,282,013 | B1 | 8/2001 | Ostler et al. | |
| 6,290,382 | B1 | 9/2001 | Bourn et al. | 362/554 |
| 6,299,597 | B1 | 10/2001 | Buscemi et al. | |
| 6,306,177 | B1 | 10/2001 | Felt et al. | 623/23.6 |
| 6,319,255 | B1 | 11/2001 | Grundei et al. | |
| 6,332,894 | B1 | 12/2001 | Stalcup et al. | |
| 6,336,914 | B1 | 1/2002 | Gillespie, III | 604/165.01 |
| 6,336,930 | B1 | 1/2002 | Stalcup et al. | 606/69 |
| 6,358,252 | B1 | 3/2002 | Shapira | 606/80 |
| 6,387,098 | B1 | 5/2002 | Cole et al. | |
| 6,395,007 | B1 | 5/2002 | Bhatnagar et al. | 606/94 |
| 6,416,531 | B2 * | 7/2002 | Chen | 607/89 |
| 6,416,737 | B1 | 7/2002 | Manolagas et al. | 424/9.2 |
| 6,419,483 | B1 | 7/2002 | Adam et al. | |
| 6,423,055 | B1 | 7/2002 | Farr et al. | |
| 6,423,083 | B2 | 7/2002 | Reiley et al. | 606/192 |
| 6,425,923 | B1 | 7/2002 | Stalcup et al. | 623/23.58 |
| 6,440,444 | B2 | 8/2002 | Boyce et al. | 424/422 |
| 6,443,988 | B2 | 9/2002 | Felt et al. | 623/17.12 |
| 6,447,514 | B1 | 9/2002 | Stalcup et al. | |
| 6,458,375 | B1 | 10/2002 | Gertzman et al. | 424/423 |
| 6,478,751 | B1 | 11/2002 | Krueger et al. | 600/566 |
| 6,482,234 | B1 | 11/2002 | Weber et al. | |
| 6,485,512 | B1 | 11/2002 | Cheng | 623/1.21 |
| 6,494,883 | B1 | 12/2002 | Ferree | 606/61 |
| 6,524,251 | B2 | 2/2003 | Rabiner et al. | 600/439 |
| 6,524,313 | B1 | 2/2003 | Fassier et al. | |
| 6,551,321 | B1 | 4/2003 | Burkinshaw et al. | |
| 6,551,337 | B1 | 4/2003 | Rabiner et al. | 606/169 |
| 6,565,528 | B1 | 5/2003 | Mueller | 604/106 |
| 6,579,277 | B1 | 6/2003 | Rabiner et al. | 604/525 |
| 6,579,279 | B1 | 6/2003 | Rabiner et al. | 604/528 |
| 6,605,056 | B2 | 8/2003 | Eidenschink et al. | |
| 6,620,185 | B1 | 9/2003 | Harvie et al. | 606/232 |
| 6,623,505 | B2 | 9/2003 | Scribner et al. | |
| 6,632,235 | B2 | 10/2003 | Weikel et al. | |
| 6,648,881 | B2 | 11/2003 | KenKnight et al. | 606/32 |
| 6,652,547 | B2 | 11/2003 | Rabiner et al. | 606/129 |
| 6,652,587 | B2 | 11/2003 | Felt et al. | 623/20.16 |
| 6,660,013 | B2 | 12/2003 | Rabiner et al. | |
| 6,679,873 | B2 | 1/2004 | Rabiner et al. | 604/528 |
| 6,695,781 | B2 | 2/2004 | Rabiner et al. | 600/129 |
| 6,695,782 | B2 | 2/2004 | Ranucci et al. | 600/439 |
| 6,696,073 | B2 | 2/2004 | Boyce et al. | 424/422 |
| 6,716,216 | B1 | 4/2004 | Boucher et al. | |
| 6,719,773 | B1 | 4/2004 | Boucher et al. | 606/192 |
| 6,726,691 | B2 | 4/2004 | Osorio et al. | |
| 6,730,048 | B2 | 5/2004 | Hare et al. | 601/2 |
| 6,733,451 | B2 | 5/2004 | Rabiner et al. | 600/439 |
| 6,733,513 | B2 | 5/2004 | Boyle et al. | |
| 6,740,093 | B2 | 5/2004 | Hochschuler et al. | 606/94 |
| 6,755,862 | B2 | 6/2004 | Keynan | 623/16.11 |
| 6,783,530 | B2 | 8/2004 | Levy | |
| 6,802,835 | B2 | 10/2004 | Rabiner et al. | 604/528 |
| 6,818,018 | B1 | 11/2004 | Sawhney | 623/11.11 |
| 6,852,095 | B1 | 2/2005 | Ray | 604/93.01 |
| 6,866,678 | B2 | 3/2005 | Shenderova et al. | 607/88 |
| 6,869,442 | B2 | 3/2005 | Cheng | |
| 6,875,212 | B2 | 4/2005 | Shaolian et al. | 606/61 |
| 6,885,246 | B2 | 4/2005 | Tsutsui et al. | 330/285 |
| 6,887,246 | B2 | 5/2005 | Bhatnagar et al. | 606/94 |
| 6,887,275 | B2 | 5/2005 | Carchidi et al. | 623/17.17 |
| 6,899,713 | B2 | 5/2005 | Shaolian et al. | 606/61 |
| 6,899,719 | B2 | 5/2005 | Reiley et al. | 606/192 |
| 6,932,843 | B2 | 8/2005 | Smith et al. | |

(56) References Cited

U.S. PATENT DOCUMENTS

| | | | |
|---|---|---|---|
| 6,964,667 B2 | 11/2005 | Shaolian et al. .............. 606/99 |
| 6,979,341 B2 | 12/2005 | Scribner et al. ............. 606/192 |
| 6,981,981 B2 | 1/2006 | Reiley et al. ................ 606/192 |
| 7,001,431 B2 | 2/2006 | Bao et al. .................. 623/17.12 |
| 7,008,433 B2 | 3/2006 | Voellmicke et al. .......... 606/93 |
| 7,052,498 B2 | 5/2006 | Levy et al. .................... 606/63 |
| 7,077,865 B2 | 7/2006 | Bao et al. .................. 623/17.12 |
| 7,124,067 B2 | 10/2006 | Ascenzi ......................... 703/11 |
| 7,141,061 B2 | 11/2006 | Williams et al. ............ 623/1.11 |
| 7,144,414 B2 | 12/2006 | Harvie et al. ................ 606/232 |
| 7,153,305 B2 | 12/2006 | Johnson et al. ............... 606/90 |
| 7,156,861 B2 | 1/2007 | Scribner et al. |
| 7,156,880 B2 | 1/2007 | Evans et al. .............. 623/23.51 |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. ................ 623/20.16 |
| 7,341,601 B2 | 3/2008 | Eisermann et al. |
| 7,360,542 B2 | 4/2008 | Nelson et al. |
| 7,407,616 B2 | 8/2008 | Melikechi et al. ........... 264/494 |
| 7,419,450 B2 | 9/2008 | Ito |
| 7,427,295 B2 | 9/2008 | Ellman et al. |
| 7,465,318 B2 | 12/2008 | Sennett et al. |
| 7,547,319 B2 | 6/2009 | Segal et al. |
| 7,621,950 B1 | 11/2009 | Globerman et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim et al. |
| 8,210,729 B2 | 7/2012 | O'Leary et al. |
| 8,211,121 B1 | 7/2012 | Quinn et al. |
| 8,246,628 B2 | 8/2012 | Rabiner |
| 8,262,694 B2 * | 9/2012 | Widomski ......... A61B 17/0057 606/151 |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 8,545,499 B2 | 10/2013 | Lozier et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,460 B2 | 5/2014 | Rabiner et al. |
| 8,764,761 B2 | 7/2014 | Truckai et al. |
| 8,870,965 B2 | 10/2014 | Rabiner et al. |
| 8,906,030 B2 * | 12/2014 | Rabiner ............. A61B 17/7097 606/93 |
| 8,906,031 B2 | 12/2014 | Rabiner et al. |
| 8,915,966 B2 | 12/2014 | Rabiner et al. |
| 8,936,382 B2 | 1/2015 | O'Leary et al. |
| 8,936,644 B2 | 1/2015 | Rabiner et al. |
| 8,939,977 B2 | 1/2015 | Dipoto et al. |
| 9,005,254 B2 | 4/2015 | Rabiner et al. |
| 9,050,079 B2 | 6/2015 | Rabiner et al. |
| 9,101,419 B2 | 8/2015 | Colleran et al. |
| 9,125,706 B2 | 9/2015 | Rabiner et al. |
| 9,144,442 B2 | 9/2015 | Rabiner et al. |
| 9,179,959 B2 | 11/2015 | Rabiner et al. |
| 9,216,049 B2 | 12/2015 | Rabiner et al. |
| 9,254,156 B2 | 2/2016 | Rabiner |
| 9,254,195 B2 | 2/2016 | Rabiner et al. |
| 9,265,549 B2 | 2/2016 | Rabiner |
| 2001/0011174 A1 | 8/2001 | Reiley et al. .................... 606/86 |
| 2001/0044626 A1 | 11/2001 | Reiley et al. .................... 606/53 |
| 2002/0032444 A1 | 3/2002 | Mische |
| 2002/0082600 A1 | 6/2002 | Shaolian et al. |
| 2002/0156482 A1 | 10/2002 | Scribner et al. ................ 606/92 |
| 2002/0161373 A1 | 10/2002 | Osorio et al. |
| 2002/0165544 A1 | 11/2002 | Perren et al. |
| 2002/0198526 A1 | 12/2002 | Shaolian et al. ................ 606/61 |
| 2003/0028210 A1 | 2/2003 | Boyle et al. |
| 2003/0083642 A1 | 5/2003 | Boyd et al. |
| 2003/0105469 A1 | 6/2003 | Karmon ........................... 606/92 |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. .................. 606/192 |
| 2004/0006341 A1 | 1/2004 | Shaolian et al. ................ 606/61 |
| 2004/0024388 A1 * | 2/2004 | Altshuler ........................... 606/2 |
| 2004/0034434 A1 | 2/2004 | Evans et al. .............. 623/23.51 |
| 2004/0059333 A1 | 3/2004 | Carl et al. ...................... 606/61 |
| 2004/0059417 A1 | 3/2004 | Smith et al. |
| 2004/0092948 A1 | 5/2004 | Stevens et al. ................. 606/96 |
| 2004/0098015 A1 | 5/2004 | Weikel et al. |
| 2004/0117025 A1 | 6/2004 | Reindel ...................... 623/18.11 |
| 2004/0133280 A1 | 7/2004 | Trieu |
| 2004/0167561 A1 | 8/2004 | Boucher et al. |
| 2004/0167625 A1 | 8/2004 | Beyar et al. ................ 623/11.11 |
| 2004/0225296 A1 | 11/2004 | Reiss et al. ..................... 606/90 |
| 2004/0228142 A1 | 11/2004 | Takada et al. |
| 2004/0230309 A1 | 11/2004 | Di Mauro et al. |
| 2004/0247641 A1 | 12/2004 | Felt et al. ...................... 424/423 |
| 2005/0010231 A1 | 1/2005 | Myers ............................. 606/86 |
| 2005/0010297 A1 | 1/2005 | Watson et al. |
| 2005/0015140 A1 | 1/2005 | deBeer |
| 2005/0015148 A1 | 1/2005 | Jansen et al. |
| 2005/0018989 A1 | 1/2005 | Shimizu et al. |
| 2005/0033437 A1 | 2/2005 | Bao et al. |
| 2005/0043733 A1 | 2/2005 | Eisermann et al. |
| 2005/0043808 A1 | 2/2005 | Felt et al. .................. 623/20.14 |
| 2005/0049691 A1 | 3/2005 | Mericle et al. |
| 2005/0090901 A1 | 4/2005 | Studer |
| 2005/0119662 A1 | 6/2005 | Reiley et al. .................... 606/92 |
| 2005/0142315 A1 | 6/2005 | DeSimone et al. .......... 428/36.9 |
| 2005/0149022 A1 | 7/2005 | Shaolian et al. ................ 606/61 |
| 2005/0159749 A1 | 7/2005 | Levy et al. ..................... 606/72 |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 * | 10/2005 | Burwell et al. ............... 600/408 |
| 2005/0234453 A1 | 10/2005 | Shaolian et al. ................ 606/61 |
| 2005/0251140 A1 | 11/2005 | Shaolian et al. ................ 606/61 |
| 2005/0284485 A9 | 12/2005 | Nelson et al. ................. 128/848 |
| 2006/0009550 A1 | 1/2006 | Messersmith et al. ......... 524/17 |
| 2006/0015105 A1 | 1/2006 | Warren et al. |
| 2006/0036253 A1 | 2/2006 | Leroux et al. .................. 606/73 |
| 2006/0084985 A1 | 4/2006 | Kim |
| 2006/0100547 A1 | 5/2006 | Rabiner et al. .................. 601/2 |
| 2006/0100635 A1 | 5/2006 | Reiley et al. .................... 606/90 |
| 2006/0100706 A1 | 5/2006 | Shadduck et al. .......... 623/17.11 |
| 2006/0111726 A1 | 5/2006 | Felt et al. ........................ 606/86 |
| 2006/0122625 A1 | 6/2006 | Truckai et al. |
| 2006/0142747 A1 | 6/2006 | Appling |
| 2006/0155296 A1 | 7/2006 | Richter ........................... 606/94 |
| 2006/0173464 A1 * | 8/2006 | Ellman et al. ................... 606/93 |
| 2006/0183811 A1 | 8/2006 | Melikechi et al. .............. 522/2 |
| 2006/0184246 A1 | 8/2006 | Zwirkoski .................. 623/11.11 |
| 2006/0195165 A1 | 8/2006 | Gertner et al. ................ 607/86 |
| 2006/0217747 A1 | 9/2006 | Ferree ........................... 606/151 |

(56) References Cited

U.S. PATENT DOCUMENTS

| | | | |
|---|---|---|---|
| 2006/0229617 A1 | 10/2006 | Meller et al. .................... 606/62 |
| 2006/0229625 A1 | 10/2006 | Truckai et al. |
| 2006/0247787 A1 | 11/2006 | Rydell et al. ............... 623/21.11 |
| 2006/0253102 A1 | 11/2006 | Nance et al. ................... 604/525 |
| 2006/0253200 A1 | 11/2006 | Bao et al. |
| 2006/0258981 A1 | 11/2006 | Eidenschink |
| 2006/0264950 A1 | 11/2006 | Nelson et al. .................... 606/72 |
| 2006/0264951 A1 | 11/2006 | Nelson et al. .................... 606/72 |
| 2006/0264952 A1 | 11/2006 | Nelson et al. .................... 606/72 |
| 2006/0265077 A1 | 11/2006 | Zwirkoski ................. 623/17.16 |
| 2006/0271024 A1 | 11/2006 | Gertner et al. |
| 2006/0271061 A1 | 11/2006 | Beyar et al. .................. 606/105 |
| 2006/0276793 A1 | 12/2006 | Berry |
| 2006/0276819 A1 | 12/2006 | Osorio et al. .................. 606/192 |
| 2006/0282169 A1 | 12/2006 | Felt et al. ................... 623/20.11 |
| 2006/0287730 A1 | 12/2006 | Segal et al. |
| 2007/0027547 A1 | 2/2007 | Rydell et al. ............... 623/21.18 |
| 2007/0067032 A1 | 3/2007 | Felt et al. ................... 623/14.12 |
| 2007/0087031 A1 | 4/2007 | Ashman et al. |
| 2007/0100327 A1* | 5/2007 | Smith ................................ 606/4 |
| 2007/0104416 A1 | 5/2007 | Shimizu et al. |
| 2007/0118143 A1 | 5/2007 | Ralph et al. ..................... 606/92 |
| 2007/0123876 A1 | 5/2007 | Czartoski et al. |
| 2007/0123877 A1 | 5/2007 | Goldin et al. ................... 606/62 |
| 2007/0123878 A1 | 5/2007 | Shaver et al. |
| 2007/0161991 A1 | 7/2007 | Altarac et al. |
| 2007/0198023 A1 | 8/2007 | Sand et al. ....................... 606/92 |
| 2007/0225705 A1 | 9/2007 | Osorio et al. .................... 606/60 |
| 2007/0233146 A1 | 10/2007 | Henniges et al. |
| 2007/0255287 A1 | 11/2007 | Rabiner ............................ 606/94 |
| 2008/0015500 A1 | 1/2008 | Herweck et al. |
| 2008/0019657 A1 | 1/2008 | Maitland et al. |
| 2008/0021474 A1 | 1/2008 | Bonutti et al. |
| 2008/0039854 A1* | 2/2008 | Rabiner ............................ 606/92 |
| 2008/0080205 A1 | 4/2008 | Forrester et al. |
| 2008/0103505 A1 | 5/2008 | Fransen ............................ 606/92 |
| 2008/0125784 A1 | 5/2008 | Rabiner et al. .................. 606/92 |
| 2008/0154266 A1 | 6/2008 | Protopsaltis et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188805 A1 | 8/2008 | Davies et al. |
| 2008/0188858 A1 | 8/2008 | Luzzi et al. ..................... 606/94 |
| 2008/0234820 A1 | 9/2008 | Felt et al. ................... 623/14.12 |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburner et al. |
| 2008/0308753 A1 | 12/2008 | Stuba et al. |
| 2009/0005782 A1 | 1/2009 | Chirico et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0076610 A1 | 3/2009 | Afzal et al. |
| 2009/0093887 A1 | 4/2009 | Walter et al. |
| 2009/0118833 A1 | 5/2009 | Hudgins et al. |
| 2009/0125028 A1 | 5/2009 | Teisen et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1 | 12/2009 | Tilson et al. |
| 2010/0076503 A1 | 3/2010 | Beyar et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0077651 A1 | 3/2011 | Lozier et al. |
| 2011/0082504 A1 | 4/2011 | Singhatat et al. |
| 2011/0098713 A1 | 4/2011 | Rabiner et al. |
| 2011/0110114 A1 | 5/2011 | Papac et al. |
| 2011/0112588 A1 | 5/2011 | Linderman et al. |
| 2011/0118740 A1 | 5/2011 | Rabiner et al. |
| 2011/0137317 A1 | 6/2011 | O'Halloran et al. |
| 2011/0160870 A1 | 6/2011 | Baumgartner et al. |
| 2011/0166306 A1 | 7/2011 | Stansbury et al. |
| 2011/0218826 A1 | 9/2011 | Birtel et al. |
| 2011/0268866 A1 | 11/2011 | Parker |
| 2011/0288522 A1 | 11/2011 | Hollowell et al. |
| 2011/0313356 A1 | 12/2011 | Rabiner et al. |
| 2012/0016371 A1 | 1/2012 | O'Halloran et al. |
| 2012/0029102 A1 | 2/2012 | Rose et al. |
| 2012/0041557 A1 | 2/2012 | Frigg |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1 | 12/2012 | Renganath et al. |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2014/0018806 A1 | 1/2014 | Dipoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2015/0066028 A1* | 3/2015 | Rabiner ............. A61B 17/7097 606/63 |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |
| 2015/0374498 A1 | 12/2015 | Rabiner et al. |
| 2016/0022333 A1 | 1/2016 | Rabiner et al. |

FOREIGN PATENT DOCUMENTS

| | | | |
|---|---|---|---|
| JP | 2001-527437 | 12/2001 | |
| JP | 2004-526525 | 9/2002 | |
| JP | 2005-511143 | 4/2005 | |
| JP | 2006-212425 | 8/2006 | |
| NL | 9001858 | 3/1992 | |
| WO | WO 98/38918 | 9/1998 | |
| WO | WO9943266 | 9/1999 | |
| WO | 0230338 | 4/2002 | |
| WO | WO 02/43628 | 6/2002 | |
| WO | WO 03/047472 | 6/2003 | |
| WO | WO 2004/045393 | 6/2004 | |
| WO | WO 2004/058045 | 7/2004 | |
| WO | WO 2004/073563 | 9/2004 | |
| WO | WO 2004/112661 | 12/2004 | ................. 17/88 |
| WO | WO 2005/112804 | 12/2005 | ................. 17/72 |
| WO | WO 2006/016807 | 2/2006 | |
| WO | WO2007002251 | 1/2007 | |
| WO | WO 2007/059259 | 5/2007 | |
| WO | WO 2007/075375 | 7/2007 | |
| WO | WO 2007/127255 | 11/2007 | |

(56) References Cited

FOREIGN PATENT DOCUMENTS

| WO | WO 2007/0127260 | 11/2007 | ............... A61F 2/00 |
|---|---|---|---|
| WO | 2008021972 | 2/2008 | |
| WO | WO 2008/039811 | 4/2008 | |
| WO | WO 2008/063265 | 5/2008 | |
| WO | WO 2009/059090 | 5/2009 | |
| WO | WO 2009/064847 | 5/2009 | |
| WO | WO 2009/082688 | 7/2009 | |
| WO | WO2009088927 | 7/2009 | |
| WO | WO 2009/131999 | 10/2009 | |
| WO | WO 2010/050965 | 5/2010 | |
| WO | WO 2010/118158 | 10/2010 | |
| WO | WO 2011/060062 | 5/2011 | |
| WO | 2011066522 | 6/2011 | |
| WO | WO 2011/071567 | 6/2011 | |
| WO | WO 2011/162910 | 12/2011 | |
| WO | WO2011162910 | 12/2011 | |
| WO | WO2012051312 | 4/2012 | |
| WO | WO 2012/088432 | 6/2012 | |
| WO | WO 2013/013069 | 1/2013 | |
| WO | WO 2013/013071 | 1/2013 | |
| WO | WO 2013/013072 | 1/2013 | |
| WO | WO2013/059609 | 4/2013 | |
| WO | WO2014011669 | 1/2014 | |
| WO | WO 2014/100427 | 6/2014 | |

OTHER PUBLICATIONS

Office Action in U.S. Appl. No. 11/789,906 mailed Mar. 11, 2010.
Office Action in U.S. Appl. No. 11/789,906 mailed Apr. 30, 2010.
Office Action in U.S. Appl. No. 11/789,907 mailed May 11, 2010.
Office Action in U.S. Appl. No. 11/903,123 mailed Jul. 1, 2010.
Office Action in U.S. Appl. No. 12/262,411 mailed Sep. 1, 2010.
PCT International Search Report based on PCT/US11/38389 dated Sep. 22, 2011.
USPTO Office Action in U.S. Appl. No. 11/964,370 mailed Sep. 23, 2011.
USPTO Office Action in U.S. Appl. No. 12/858,924 mailed Oct. 24, 2011.
USPTO Office Action in U.S. Appl. No. 12/755,784 mailed Dec. 23, 2011.
USPTO Office Action in U.S. Appl. No. 12/886,288 mailed Dec. 27, 2011.
Office Action in U.S. Appl. No. 11/964,370 mailed Dec. 9, 2010.
International Search Report based on PCT/US10/56219 dated Jan. 20, 2011.
Jovanovic et al., *Fixion Nails for Humeral Fractures*, Injury, Int. J. Care Injured, vol. 34, Issue 11, pp. 1140-1142, Nov. 2004.
Maruyama et al., *Metacarpal Fracture Fixation with Absorbable Polyglycolide Rods and Stainless Steel K Wires: A Biomechanical Comparison*, Journal of Biomedical Materials Research (Applied Biomaterials), vol. 33, pp. 9-12, 1996.
Waris et al., Bioabsorbable Miniplating Versus Metallic Fixation for Metacarpal Fractures, Clinical Orthopaedics and Related Research, No. 410, pp. 310-319, May 2003.
Waris et al., *Self-Reinforced Bioabsorbable Versus Metallic Fixation Systems for Metacarpal and Phalangeal Fractures: A Biomechanical Study*, The Journal of Hand Surgery, vol. 27A, No. 5, pp. 902-909, Sep. 2002.
PCT International Search Report based on PCT/US07/20402 dated Apr. 1, 2008.
PCT International Search Report based on PCT/US07/10050 dated Apr. 17, 2008.
PCT International Search Report based on PCT/US07/10038 dated Aug. 27, 2008.
International Search Report based on PCT/US08/81929 dated Jan. 12, 2009.
International Search Report based on PCT/US08/81924 dated Feb. 9, 2009.
International Search Report based on PCT/US08/87630 dated Feb. 24, 2009.
Office Action in U.S. Appl. No. 11/789,906 mailed Apr. 29, 2009.
PCT International Search Report based on PCT/US11/66871 dated May 1, 2012.
USPTO Office Action in U.S. Appl. No. 12/875,460 mailed Mar. 8, 2012.
USPTO Office Action in U.S. Appl. No. 11/964,370 mailed Mar. 16, 2012.
USPTO Office Action in U.S. Appl. No. 12/858,924 mailed Apr. 4, 2012.
USPTO Office Action in U.S. Appl. No. 12/756,014 mailed May 11, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/859,680 mailed Jan. 17, 2013.
PCT International Search Report for PCT/US2012/061047 mailed Jan. 7, 2013.
USPTO Office Action in U.S. Appl. No. 12/756,014 mailed Jan. 22, 2013.
USPTO Office Action in U.S. Appl. No. 13/088,916 mailed Jan. 23, 2013.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 13/088,916 mailed May 13, 2013.
USPTO Office Action in U.S. Appl. No. 13/772,947 mailed Jun. 19, 2013.
USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.
USPTO Office Action in U.S. Appl. No. 12/943,544 mailed Sep. 25, 2013.
USPTO Office Action in U.S. Appl. No. 13/617,557 mailed Oct. 9, 2013.
Extended European Search Report based on EP 10 76 2390 dated Oct. 30, 2013.

(56) References Cited

OTHER PUBLICATIONS

USPTO Office Action in U.S. Appl. No. 12/983,496 mailed Feb. 5, 2014.
USPTO Office Action in U.S. Appl. No. 12/756,014 mailed Feb. 13, 2014.
USPTO Office Action in U.S. Appl. No. 13/617,181 mailed Feb. 25, 2014.
PCT International Search Report based on PCT/US13/076598 dated Mar. 19, 2014.
USPTO Office Action in U.S. Appl. No. 13/655,808 mailed Mar. 27, 2014.
USPTO Office Action in U.S. Appl. No. 13/553,247 mailed May 7, 2014.
Extended European Search Report based on EP 14156473 dated May 13, 2014.
USPTO Office Action in U.S. Appl. No. 13/800,518 mailed Jun. 10, 2014.
USPTO Office Action in U.S. Appl. No. 13/617,557 mailed Jun. 27, 2014.
USPTO Office Action in U.S. Appl. No. 13/335,110 mailed Jul. 31, 2014.
USPTO Office Action in U.S. Appl. No. 13/616,781 mailed Aug. 26, 2014.
USPTO Office Action in U.S. Appl. No. 13/730,521 mailed Sep. 8, 2014.
PCT International Search Report based on PCT/US13/049773 dated Oct. 1, 2013.
USPTO Office Action in U.S. Appl. No. 12/756,014 mailed Oct. 7, 2014.
USPTO Office Action in U.S. Appl. No. 13/553,450 mailed Oct. 24, 2014.
USPTO Office Action in U.S. Appl. No. 13/335,110 mailed Oct. 24, 2014.
USPTO Office Action in U.S. Appl. No. 13/553,247 mailed Dec. 5, 2014.
USPTO Office Action in U.S. Appl. No. 13/553,051 mailed Dec. 23, 2014.
USPTO Office Action in U.S. Appl. No. 13/617,557 mailed Jan. 15, 2015.
USPTO Office Action in U.S. Appl. No. 13/335,110 mailed Feb. 9, 2015.
USPTO Office Action in U.S. Appl. No. 13/796,085 mailed Feb. 12, 2015.
USPTO Office Action in U.S. Appl. No. 13/553,051 mailed Mar. 31, 2015.
USPTO Office Action in U.S. Appl. No. 13/553,051 mailed Sep. 11, 2015.
USPTO Office Action in U.S. Appl. No. 13/553,247 mailed Sep. 23, 2015.
USPTO Office Action in U.S. Appl. No. 14/164,846 mailed Oct. 14, 2015.
USPTO Office Action in U.S. Appl. No. 14/171,036 mailed Oct. 15, 2015.
USPTO Office Action in U.S. Appl. No. 13/796,085 mailed Nov. 27, 2015.
USPTO Office Action in U.S. Appl. No. 13/553,051 mailed Jan. 6, 2016.
USPTO Office Action in U.S. Appl. No. 13/617,557 mailed Jan. 14, 2016.
USPTO Office Action in U.S. Appl. No. 14/177,748 mailed Jan. 25, 2016.
USPTO Office Action in U.S. Appl. No. 14/535,913 mailed Feb. 22, 2016.
USPTO Office Action in U.S. Appl. No. 13/553,247 mailed Mar. 2, 2016.
USPTO Office Action in U.S. Appl. No. 14/535,971 mailed Mar. 4, 2016.
USPTO Office Action in U.S. Appl. No. 13/553,247 mailed May 1, 2015.
USPTO Office Action in U.S. Appl. No. 13/297,097 mailed May 29, 2015.
USPTO Office Action in U.S. Appl. No. 14/171,036 mailed Jun. 1, 2015.
USPTO Office Action in U.S. Appl. No. 14/164,846 mailed Jun. 4, 2015.
USPTO Office Action in U.S. Appl. No. 13/617,557 mailed Jul. 15, 2015.
USPTO Office Action in U.S. Appl. No. 13/796,085 mailed Jul. 17, 2015.
International Search Report based on PCT/US10/46003 dated May 24, 2011.
Final Office Action in U.S. Appl. No. 11/964,370 mailed Apr. 28, 2011.

* cited by examiner

LIGHT SOURCE

RELATED APPLICATIONS

This application is related to and claims the benefit of priority from U.S. Provisional Patent Application No. 60/984,241, filed on Oct. 31, 2007, the entirety of which is incorporated herein by reference.

FIELD

The embodiments disclosed herein relate to light sources, and more particularly to disposable light sources for providing light to a remote location.

BACKGROUND

Light sources are used in medical procedures for a variety of purposes including illuminating dark or poorly lit regions, heating, burning, ablating and/or destroying tissue, organs, vessels or other body structures, curing materials, such as glues or epoxies, and a variety of other uses. Different frequencies, bandwidths or colors of light are oftentimes used for different medical applications. For example, white light may be used for general screening of a patient and blue or ultra violet light may be used to cure certain glues or epoxies.

Typical light sources are large electronic devices which sit outside the sterile environment and are connected into the sterile field by a cord or lightpipe. The lightpipe is sterilized between uses which the light source remains outside of the sterile environment and need not be sterilized. Configuring the light source so that the base may remain outside of the sterile environment, long cords are required to allow the user to manipulate the light with respect to the patient. Longer cords result in a greater chance that the cord will become tangled, that medical personnel might trip over the cord, that the cord will get in the way of other instruments or cords and a variety of other risk factors.

The light sources are powered by electricity, typically 110-220 volts of indirect current coming from a wall socket. The light sources are physically tied to the wall socket by a power cord and depend upon a building's electricity system for power. This dependency upon the electrical system can cause problems if the electricity is compromised or stopped, for example during a power outage. In addition, the movement of the light source within the operating suites, or other medical room, is constrained by the cord and the device can only be moved so far without unplugging the light source and replugging into a closer wall socket, if one exists, or the use of extension cords. In addition, current light sources need to be regularly serviced and often repaired as the light sources are used for multiple patients.

Thus, there is a need in the art for a disposable light source as described herein.

SUMMARY

Disposable light sources are disclosed herein. In some embodiments the light sources may be smaller and/or more efficient than the prior art and may satisfy the need for an emergency system (e.g., in case of a power failure or in a location where power is difficult to access or inaccessible) where light can generated using a 12-volt or other voltage system. According to aspects illustrated herein, there is provided a disposable apparatus for providing light including a light source, a light director to focus light from the light source, the light director surrounding at least a portion of the light source, a power source providing energy to the light source, and a connector communicating light from the light source to a catheter.

According to aspects illustrated herein, there is provided a device for connecting a fiber to a light source including a light source for emitting light in at least a first direction, a light director surrounding at least a portion of the light source, the light director having a face substantially perpendicular to the first direction and having an inner surface including a light reflecting media, and a connector extending from the light director, the connector being positioned such that when an end of a fiber is inserted into the connector, the end of the fiber is correctly aligned with the face of the light director.

According to aspects illustrated herein, there is provided a system for delivering light to remote location including a light source, an expandable device for insertion into a bone, and a fiber for communicating light from the light source to the expandable device.

According to aspects illustrated herein, there is provided a method of delivering light from a disposable light source to a remote location including delivering a bone reinforcing mixture into a cavity of a bone at a remote location through a catheter, positioning a fiber connected to a disposable light source proximate the remote location, communicating light from the disposable light source to the remote location through the fiber, curing the bone reinforcing mixture in the cavity of the bone with light emitted from the disposable light source, and discarding the disposable light source after a single use.

Various embodiments provide certain advantages. Not all embodiments of the invention share the same advantages and those that do may not share them under all circumstances. Further features and advantages of the embodiments, as well as the structure of various embodiments are described in detail below with reference to the accompanying drawings.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments. For purposes of clarity, not every component is labeled in every drawing. In the drawings.

Figure 1:
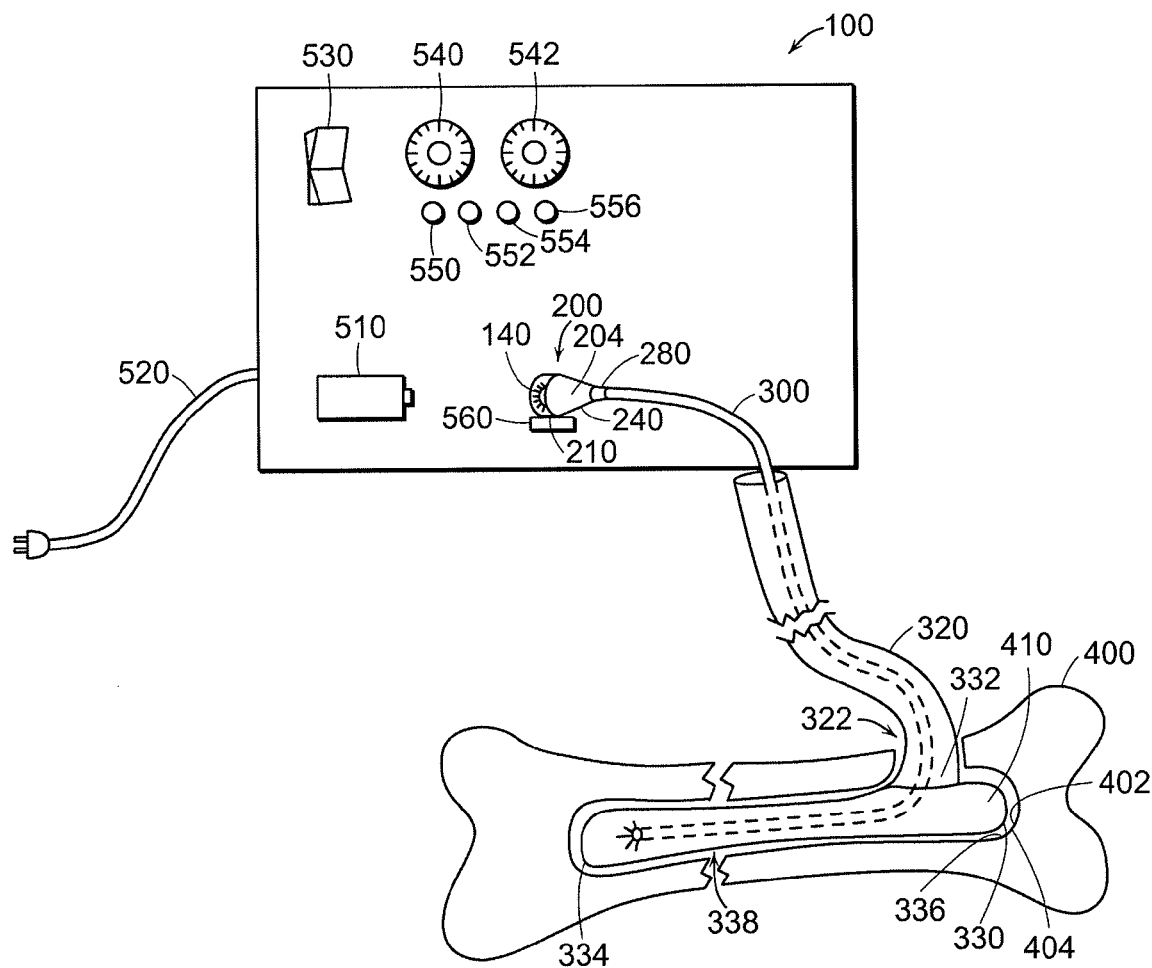
FIG. 1 is a perspective view of an illustrative embodiment of a disposable apparatus and a bone with a balloon and catheter therein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The inventions are not limited in its application to the details of construction and the arrangement of components set forth in the following description or illustrated in the drawings. The inventions are capable of being arranged in other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Aspects of the inventions are described below with reference to illustrative embodiments. It should be understood that reference to these illustrative embodiments is not made to limit aspects of the inventions in any way. Instead, illustrative embodiments are used to aid in the description and understanding of various aspects of the inventions. Therefore, the following description is intended to be illustrative, not limiting.

Embodiments of the present invention are directed to a disposable apparatus. As shown in the embodiment of FIG. 1, the disposable apparatus 100 may have a light source 140 and a connector 280. An optical fiber 300 may be inserted into the connector 280 to communicate light from the light source 140 to a remote location, such as a cavity 402 within a bone 400. The light may be used to cure a substance, such as a bone reinforcing mixture 410.

In some embodiments, the optical fibers 300 may be inserted into a catheter 320 with a balloon 330 connected to the distal end 322 of the catheter 320. The balloon 330 may be positioned in the cavity 402 in the bone 400 and bone reinforcing material 410, such as a glue or epoxy, is inserted into the balloon 330 via the catheter 320. The optical fibers 300 delivers light into the balloon 330 to cure the bone reinforcing material 410.

To funnel a greater amount of light from the light source 140 into the optical fibers 300, the light from the light source 140 may be reflected into a smaller area by using a light director 200. The light director 200 may include a ring 210 and/or an optical taper 240 containing a light reflective media 204 to direct the light from a larger diameter to a smaller diameter.

Power for the light source 140 and other parts of the disposable apparatus 100 may be provided by a power source, such as a battery 510 and/or a power cord 520. An on/off switch 530 may control the flow of power to the light source 140 and timers 540, 542 and/or pulse buttons 550, 552, 554, 556 may be included to allow a user to precondition the application of light. A heat sink 560 may be located near the light source 140 to draw excess heat off the light source 140.

The light source 140 may be a light emitting diode (LED) that emits light at a certain wavelength. The light source 140 may contain a second LED or a third LED which emit light at different wavelengths. The wavelength(s) of light emitted by the light source(s) may depend on the substance to be cured. In some embodiments, the light source 140 may be more efficient and/or smaller than previously available light sources.

In some embodiments, the apparatus is disposable, such that the apparatus is to be discarded after one use rather than cleaned, sterilized and reused. The disposable apparatus may be discarded after a single procedure or after use with a single patient.

It may be desirable to provide or manufacture the disposable apparatus so that it is not harmful to the environment. For example, the disposable apparatus may be made of a recyclable composition. The disposable apparatus may also or alternatively be made of a biodegradable composition, or a composition that is otherwise easily broken down by mechanical energy, heat energy, or any other recycling technique. The disposable apparatus may also be made of a composition that is free from toxic chemicals, environmental pollutants, or other harmful materials.

The disposable apparatus may be designed for use in a medical setting. For example, the disposable apparatus may be used in a doctor's office, hospital, veterinarian's office, or other location of medical examination or procedures. Accordingly, it may be desirable that the container be sterile, e.g., formed from a sterile material in a sterile environment or formed from a composition that is sterilizable. For example, the disposable apparatus may be formed from a composition that can be sterilized or disinfected, through chemical, heat, or electromagnetic treatment, or any other treatment sufficient to sterilize or disinfect the disposable apparatus. It should be appreciated that the disposable apparatus may employ a wider variety of materials and structural designs as the disposable apparatus need not be resterilized or disinfected a second time. The disposable apparatus may also be arranged so as not to interfere with medical equipment and procedures. For example, the disposable apparatus may be formed from a composition or otherwise arranged so as not to interfere with medical equipment or radiation, such as X-rays used for imaging or medical lasers used for treatment. The disposable apparatus may also be made of a composition or arranged so as to be chemically unreactive and free from hazardous materials so as not to be dangerous to patients or medical personnel. Hospital fire codes often require the use of non-flammable and heat resistant materials. Thus, the disposable apparatus may also be constructed from non-flammable materials or compositions. For example, the disposable apparatus may be made of a composition that is latex-free so as to be compatible with a latex-free surgical environment.

It should be appreciated that the disposable apparatus and the components thereof may be formed in any suitable manner and with any suitable materials as not all embodiments are intended to be limited in this manner.

The disposable apparatus includes a light source to provide light energy. In some embodiments, the light source may deliver a high intensity light, may produce more light per watt than an incandescent bulb (as may be useful for battery powered or energy saving devices), may emit a light of an intended color without the use of color filters, may have a structure which focuses its light, may not change its color tint as the current passing through the light source is lowered, may not burn out more quickly when cycled on and off frequently, may be resistant to damage from external shocks, may have an extremely long life span, such as between 100,000 and 1,000,000 hours, may fail by dimming over time, may light up quickly, such as by achieving full brightness in microseconds, may be very small, may be easily populated on printed circuit boards and/or may not contain mercury. In some embodiments, the light source is a light emitting diode (LED), such as an organic light-emitting diode, polymer light emitting diode, solid-state lighting or an LED lamp.

An LED is a semiconductor device that emits light through electroluminescence. An LED is a special type of semiconductor diode. Like a normal diode, an LED consists of a chip of semiconducting material impregnated, or doped, with impurities to create a structure called a pn junction. Charge-carriers (electrons and holes) are created by an electric current passing through the junction. When an electron meets a hole, it falls into a lower energy level, and releases energy in the form of light.

LEDs emit incoherent quasi-monochromatic light when electrically biased in the forward direction. The color of light emitted depends on the semiconducting material used and can be near-ultraviolet, visible, or infrared. The wavelength of the light emitted, and therefore its color, depends on the bandgap energy of the materials forming the pn junction. A normal diode, typically made of silicon or germanium, emits invisible far-infrared light, but the materials used for an LED have bandgap energies corresponding to near-infrared, visible, or near-ultraviolet light.

The electromagnetic spectrum is the range of all possible electromagnetic radiation. The electromagnetic spectrum of an object is the frequency range of electromagnetic radiation that it emits, reflects, or transmits. The electromagnetic spectrum extends from just below the frequencies used for modern radio (at the long-wavelength end) to gamma radiation (at the short-wavelength end), covering wavelengths from thousands of kilometers down to fractions of the size of an atom. Ultraviolet (UV) light wavelength ranges from about 1 nm to about 380 nm, and can be subdivided into the following categories: near UV (380-200 nm wavelength; abbreviated NUV), far or vacuum UV (200-10 nm; abbreviated FUV or VUV), and extreme UV (1-31 nm; abbreviated EUV or XUV). Similarly, visible light has a wavelength spectrum of between about 380 to about 780 nm.

Depending on the intended use of the light, an LED emitting a specific wavelength may be chosen. For example, if the intended use of the light is curing a UV-curable bone reinforcing material, the LED may emit light at a wavelength between about 400 and about 470 nanometers. In particular, the LED may emit light at a wavelength of about 390-420 nanometers, 450 nanometers (royal blue), about 460 nanometers and/or about 470 nanometers. It should be appreciated that the light source may emit any wavelength of light, visible (about 380 nanometers to about 780 nanometers) or outside the visible spectrum (less than 380 nanometers or greater than 780 nanometers), as not all embodiments are intended to be limited in this respect.

In some embodiments, the light wavelength may be about 450 nm (similar to Blue Wave™ 200, commercially available from DYMAX Corporation of Torrington, Conn.), which is above UV light and specific eye protection may not be necessary. In addition, filters may be added to inhibit all UV below about 400 nm.

In some embodiments, the light source 140 may employ commercially available materials, may include 5 mm diameter diodes, may have a high intensity, such as about 5 to about 50 watts and/or may overdrive the light source 140 for maximum illumination output, possibly at the expense of useful life of the light source 140.

The light source may be another type of diode, electroluminescent lamp, a gas discharge lamp, (such as a fluorescent lamp including a compact fluorescent lamp and a black light, inductive lighting, a hollow cathode lamp, a neon lamp, an argon lamp, a plasma lamp or a xenon flash lamp), a chemoluminescent source, fluorescent source, phosphorescent source, a combustion-based source, an electric source, an incandescent lamp, a high-intensity discharge lamp, a nuclear source, a laser, or any other type of light source as not all embodiments of the present invention are intended to be limited in this manner.

The light source 140 may include a first light source 150 and a second light source 160. To provide light that covers a wider range of wavelengths over which a potential polymer or epoxy may cure, the second light source 160 may emit a second light at a different wavelength than the light emitted by the first light source 150. In some embodiments, the different wavelengths may each assist in curing a single substance. In some embodiments, each wavelength may assist in curing different substances or different portions of one substance. In some embodiments, the light source 140 includes a third, fourth or more light sources emitting light having a similar or differing wavelength compared to one another, as not all embodiments are intended to be limited in these respects.

Figure 2:
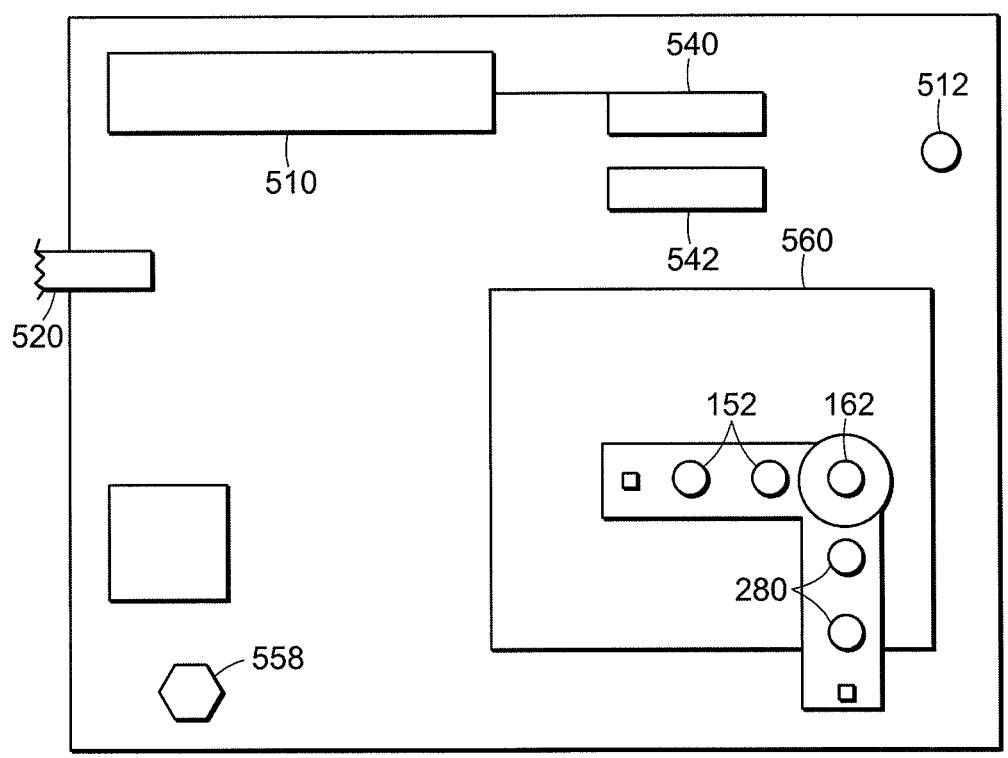
FIG. 2 is a cross-sectional view of an illustrative embodiment of a disposable apparatus.

In some embodiments, such as the embodiment depicted in FIG. 2, the disposable apparatus 100 may have three light sources, two UV emitting LEDs 152 and one visible light emitting LED 162. Those skilled in the art will appreciate that different combinations of LEDs may be used and still be within the spirit and scope of the present invention.

To assist in focusing light from the light source, a collimator or a light director 200 may be employed. The light director 200 may include a ring 210 that surrounds at least a portion of the light source 140 to concentrate the light. The ring 210 may have a ring-like shape, but may also have other shapes, such as a toroid, torus, ellipsoid, and/or spheroid, and may also have any curvature of the walls of the ring, such as straight, concave, convex, angled, any other configuration and/or any combination thereof, as not all embodiments are intended to be limited in this respect, nor is the word "ring" intended to impart structural limitations into all embodiments. For example, in some embodiments, such as is depicted in the embodiment shown in FIG. 4, the ring 210 may have curved walls or a tulip-like shape, acting to focus light emitted from the light source 140. In some embodiments, the ring 210 may circumvent at least a majority of the outer edge 142 of the light source 140, while in some embodiments, the ring 210 may completely encircle the light source 140.

Figure 3:
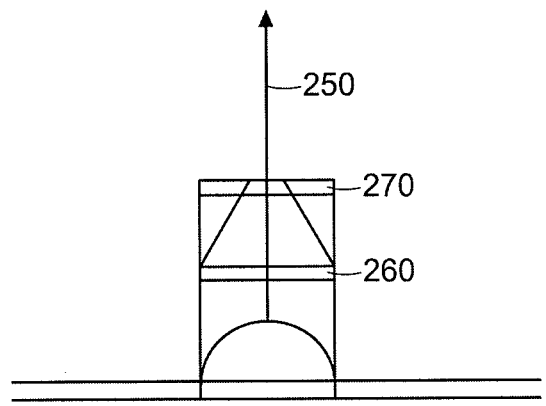
FIG. 3 is a cross-sectional view of an illustrative embodiment of a light source and a light director.
Figure 4:
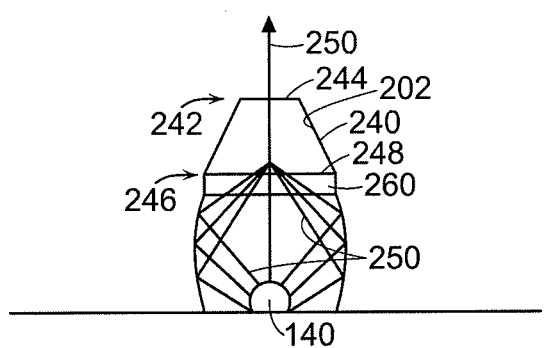
FIG. 4 is a cross-sectional view of an illustrative embodiment of a light source and a light director.
Figure 5:
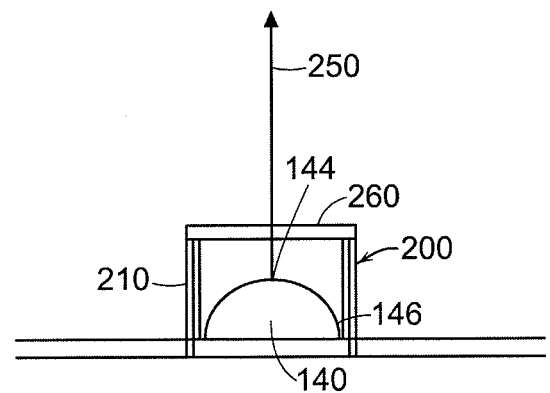
FIG. 5 is a cross-sectional view of an illustrative embodiment of a light source and a light director.

As shown in FIG. 3, FIG. 4 and FIG. 5, the ring 210 may surround a distal end 144 of the light source 140. In some embodiment, the light director may abut a distal end of the light source and may not cover any portion of the sides of the light source. In other embodiments, the ring 210 may partially or completely cover the sides 146 of the light source 140.

The light director 200 may also include an optical taper 240 for further focusing the light from the light source, for example, by taking a larger diameter of light and forcing it down into a smaller diameter to produce a more focused beam. Light emitted from some light sources, such as some LEDs, may be domed. It may be desirable to redirect the non-central light from a domed light emitting light source into a central path. In some embodiments, such as those with optical fibers having a smaller diameter, the light director may be more necessary than those with optical fibers having a larger diameter. A tapered, reflective wall assists in directing non-central light into a central path. By having an inward tilt on a mirrored or reflective surface, the light hitting the tapered distance may be shortened, allowing more light to hit the center of the taper. In some embodiments, the optical taper 240 may have a conical frustum shape (a cone with the top sliced off to create a second face parallel to the base). The optical taper 240 may have a first end 242 distal to the light source 140, the first end 242 having a first face 244 substantially perpendicular to the direction 250 of the light emitted from the light source 140. The optical taper 240 may have a second end 246 proximate the light source 140, the second end 246 having a second face 248 substantially perpendicular to the direction 250 of the light emitted from the light source 140 and substantially parallel to the first face 244.

The light director 200 may further include lenses 260, 270 between the various parts of the light director 200. In some embodiments, as depicted in FIG. 3, FIG. 4 and FIG. 5, lens 260 may be inserted between the ring 210 and the optical taper 240 and lens 270 may be located adjacent the first end 242 of the optical taper 240. The lenses may have any shape depending on the desired effect of each lens. In some embodiments, at least one and or both of the lenses 260, 270 are plano lenses (e.g., flat lenses) or concave-convex lenses (having the same degree of curvature on both the concave and convex sides) with no vergence and do not bend the light passing therethrough. In some embodiments, at least one or both of the lenses are plano-convex, biconvex or concave-convex (having a greater degree of curvature on the convex side than on the concave side) lenses causing the light to converge. In some embodiments, the lens or lenses may serve to redirect the focal point of the light, for example, moving the focal point closer to or farther from the lens or light source. At least one or both of the lenses 260, 270 may have any combination of plano, convex and concave sides of the lenses as not all embodiments of the present invention are intended to be restricted in this manner.

In addition, some embodiments of the light director 200 may include an optical glue to engage the parts to one another. Examples of optical glues include, but are not limited to, those available from Master Bond Inc of Hackensack, N.J. or Epotec® Epoxies available from the Epoxy Division of Aditya Birla Chemicals of Bangkok, Thailand.

In some embodiments a liquid or water bushing may be employed between faces. A space between the faces may be filled with an optically clear liquid which may be contained within a balloon, such as a balloon made from polyethylene terephthalate (PET).

To further provide an optically clear service between the parts, the abutting surfaces may be polished before being joined. In addition, other means of providing an optically clear connection between two pieces may be employed to further a clear connection, as not all embodiments are intended to be limited in this manner.

In some embodiments, the light director 200 may include a light reflecting media 204. The light reflecting media may be a mirror or another reflecting material, such as a metal, glass and mylars. The light reflecting media may reflect a specific wavelength of light, a range of wavelengths of light or all wavelengths of light, as not all embodiments are designed to be limiting in this respect.

In some embodiments, the light reflecting media may be arranged to cause retroreflection. Retroreflection may be accomplished using a variety of configurations. In some embodiments, a set of three mutually perpendicular mirrors which form a corner (a corner reflector or corner cube). Corner retroreflectors may be formed by a corner which is a truncated corner of a cube of transparent material such as conventional optical glass. In this structure, reflection may be achieved either by total internal reflection or by silvering of the outer cube surfaces. Corner retroreflectors may also be formed from mutually perpendicular flat mirrors bracketing an air space. These two configurations may have similar optical properties.

In some embodiments, reflecting and refracting optical elements are arranged so that the focal surface of the refractive element coincides with the reflective surface (e.g., a transparent sphere and a spherical mirror. A similar effect may be achieved with a single transparent sphere provided that the refractive index of the material is two times the refractive index of the medium from which the radiation is incident. In this embodiment, the sphere surface may behave as a concave spherical mirror with the required curvature for retroreflection. This is conventionally known as a cat's eye retroreflector.

A retroreflector may consist of many very small versions of these structures incorporated in a thin sheet or in paint. In some embodiments, paint may contain glass beads, such that the paint glues the beads to the surface where retroreflection is desired, and the beads protrude, because their diameters are about twice the thickness of the paint.

In some embodiments, retroreflector may be produced by using the nonlinear optical phenomenon of phase conjugation. This technique may be used in advanced optical systems such as high-power lasers and optical transmission lines. Phase conjugate mirrors may necessitate a comparatively expensive and complex apparatus, as well as large quantities of power (as nonlinear optical processes may be most efficient at higher intensities). However, phase conjugate mirrors may have a greater accuracy in the direction of the retroreflection, which in passive elements may be limited by the mechanical accuracy of the construction. It should be appreciated that all of the above embodiments as well as other configurations for producing retroreflection are contemplated and are within the scope of the present invention.

In some embodiments, the light reflecting media 204 may be located on an inner surface 202 of the ring 210 or optical taper 240. In some embodiments, the light director 200 may be made entirely of the light reflecting media 204 while in some embodiments the light reflecting media 204 may constitute a portion of the light director 200, as not all embodiments are intended to be limited in this respect.

As discussed above, in some embodiments the light sources includes two or more light sources. In these embodiments, each light source may have its own light directors and/or may share a light director with one or more other light sources. In some embodiments, each light source may have its own ring 210 and its own optical taper 240 surrounding at least a portion of each light source. In some embodiments, each light source may have its own ring 210 and share an optical taper designed to guide the light from each light source into a common fiber. In some embodiments, all the light sources share one light director. In some embodiments, each light source may have its own fiber communicating light from the light source to a main optical fiber or directly to the remote location. In some embodiments, some light sources may share a light director or any portion thereof, while other light sources have their own light director, as not all embodiments are intended to be limited in the above respects.

The disposable apparatus 100 may be powered by a contained or auxiliary power source. In some embodiments, an auxiliary power source, such as a power cord 520, may be used as the sole or supplementary source of power for the disposable apparatus. In order to enable the apparatus 100 to be portable and not constrained by depending on an external source of power or by tethering to a wall outlet by a power cord, in some embodiments, a portable power source, such as one or more batteries 510, may be used to power the disposable apparatus 100. In some embodiments, the battery 510 may be a disposable battery while in other embodiments, the battery 510 may be a rechargeable battery. In some embodiments the battery 510 may be one or more 9 volt batteries which could be stacked in length with an optional power resistor to inhibit overpowering. In some embodiments, the battery 510 may be enclosed within the casing of the disposable apparatus and not be removable without destroying the casing, while in some embodiments, the battery may be easily removed via a closable door or flap, as not all embodiments are intended to be limited in the preceding respects.

To control the flow of energy to the light source 140 and any other electrically powered parts of the disposable apparatus 100, the disposable apparatus 100 may have an on/off switch. In some embodiments, the disposable apparatus 100 may have a timer 540 which may be set to automatically turn off the flow of power after a certain amount of time has elapsed. In some embodiments, such as the embodiment depicted in FIG. 2, the disposable apparatus 100 may include an indicator light, such as LED 512, which lights up when the disposable apparatus 100 is on.

To allow a glue to cure in a slower fashion, so as to not over excite the glue and/or inhibit a cured crust of glue over a pool of uncured glue, the disposable apparatus 100 may have a pulse timer 542 which may be set to automatically turn off a syncopated flow of power after a certain amount of time has elapsed. In addition, the disposable apparatus 100 may have pulse buttons 550, 552, 554, 556 which may represent different pulse lengths. For example, in some embodiments, pulse button 550 may represent a pulse interval of 0.5 seconds, pulse button 552 may represent a pulse interval of 1 second, pulse button 554 may represent a pulse interval of 2 seconds, and pulse button 556 may represent a pulse interval of 5 seconds. Thus, if a user sets the pulse timer 542 for 180 seconds and chooses a pulse interval of 2 seconds, the light source will illuminate for two seconds every four seconds, for 180 seconds. In addition or alternatively, the disposable apparatus is preprogrammed to emit a predetermined amount of energy for a predetermined amount of time. It should be appreciated that the above-described embodiments are exemplary and some embodiments may allow a user to choose or may be preset to a varied sequence of timed pulses, with any amount of time for the pulse, any amount of time between pulses and any total time of exposure, as not all embodiments of the present invention are intended to be limited in these respects.

To assist a user in determining that enough time for the glue to cure has elapsed, an indicator may light up or sound. In some embodiments, the indicator may be a light on the disposable apparatus or on the optical fibers. In some embodiments, the indicator may be speaker 558 which emits a beeping sound or a voice stating, "you are now clear to detach the catheter" or any other alert. The indicator may be triggered when the glue has hardened or when a predetermined amount time has elapsed (the predetermined amount of time being set to allow sufficient curing of the glue). The settings may be predetermined and/or established by the user over time.

The functions of timing, pulsing and/or pre-programming may be accomplished by using any means, such as microprocessors, GPS timers, atomic clocks, stop watches, count down timers, other electronics, or any other device or method as not all embodiments of the present invention are intended to be limited in this respect.

Certain types for lights, such as LEDs, may generate heat. To absorb or dissipate at least a portion of heat from the light source 140, a heat sink 560 may be located proximate the light source 140. Some embodiments may include a fan (not shown) to cool the light source 140. Not all embodiments are intended to be limited in this respect and any means of cooling the light source 140 may be employed. In some embodiments, the use of a heat sink may not be desirable as the heat from the light source of another heat-producing element may be used to warm the battery to encourage the battery to fully drain. While warm batteries tend to drain faster, when this light source is utilized in a single-use application, fast drainage of the batteries may not be a concern.

Figure 6:
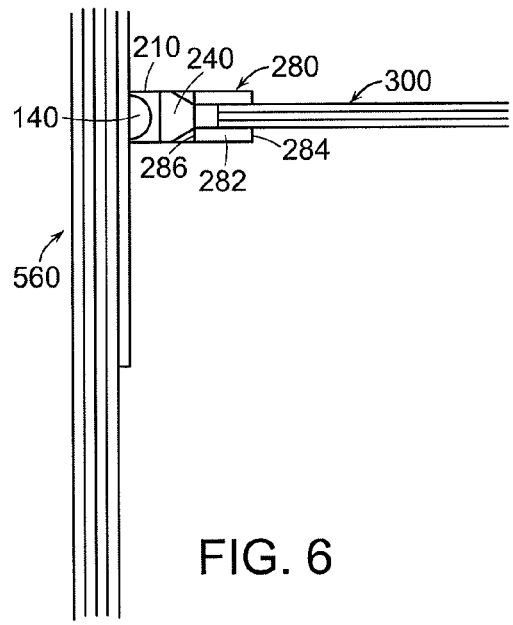
FIG. 6 is a cross-sectional view of an illustrative embodiment of components of a disposable apparatus and optical fibers.
Figure 7:
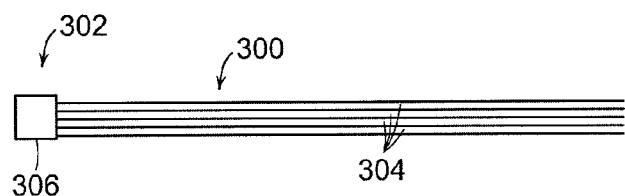
FIG. 7 is a cross-sectional view of an illustrative embodiment of optical fibers.

To connect optical fibers 300 to the light source 140, a connector 280 may be employed. As shown in the embodiments depicted in FIG. 6 and FIG. 7, the connector 280 may include an optical plug 282 into which the optical fibers 300 may be inserted. In some embodiments, an outermost surface 284 of the optical plug 282 may be flush with the disposable apparatus, while in some embodiments, the optical plug 282 may extend from the surface of the disposable apparatus. In some embodiments, the connector 280 may include a bracket or other device for supporting the optical fibers 300. The optical plug 282 may have an inner surface 286 which is contacted by an end 302 of the optical fibers 300. The inner surface 286 may be perpendicular to the direction 250 of light emitted from the light source 140 and parallel and flush with the lens 270 or the first face 244 of the light director 200.

In some embodiments, the connector 280 may include a locking mechanism for releasably locking the optical fibers 300 in the connector 280. The optical fibers may be fixedly attached or removably connected to the connector 280 or directly to the light director 200 or light source 140 as not all embodiments are intended to be limited in this respect. In some embodiments, the connector may be constructed and arranged to attach to a plurality of optical fibers. In some embodiments, multiple connectors may be employed and one or more optical fibers may attach to each of the multiple connectors. For example, the light source may have three connectors wherein a single optical fiber attaches to one of the connectors, two optical fibers attach to a second of the connectors and a bunch of more than ten optical fibers attach to the third of the connectors.

It may be desirable to correctly align the end 302 of the optical fibers 300 with the connection to the light source 140, whether the connection be part of the connector 280, such as the inner surface 286 of the optical plug 282, part of the light director 200, such as lens 270 or the first face 244 of the optical taper 240, or part of the light source 140 itself. Depending on structure of the connection and the intended use, correctly alignment may include an embodiment wherein the end 302 of the optical fibers 300 is substantially flush with an outermost face of the light director 200, an embodiment wherein a center of the end 302 of the optical fibers 300 is aligned with a center of a face of the light director 200, and/or an embodiment wherein an outermost perimeter of the end 302 of the optical fibers 300 is aligned with an outermost perimeter of the face of the light director 200. In some embodiments, the connector 280 may include an alignment ring to assist with correctly inserting the optical fibers 300.

Although "butt" joint or flush-to-flush connectors are described above, not all embodiments of the present invention are intended to be limited in this manner and other optical connections are within the scope of the present invention.

In some embodiments, the optical fibers connect with the light source without the use of a light director 200 and/or a connection 280, while in some embodiments some or all of the intermediary parts are utilized as not all embodiments of the present invention are intended to be limited in this respect. As described above with respect to the light director, any means of creating an optically clear connection between the optical fibers 300 and the connector 280, light director 200 and/or light source 140 may be employed such as an optical glue, polishing surfaces, or any other products or methods known in the art.

To communicate the light from the light source 140 to the remote location, the optical fibers 300 are employed. As shown in the embodiment depicted in FIG. 6 and FIG. 7, the optical fibers 300 may include a plurality of individual optical fibers 304 which are collected by a mechanical connector 306 at least at the end 302. The mechanical connector 306 may include, but is not limited to, a metallic ring, a polymer ring using glue or similar structures. After the optical fibers 300 are bound together, the optical fibers 300 may be cut in an even manner. The optical fibers 300 may be polished smooth to assist in pointing light illumination. In some embodiments, the optical fibers 300 include only one optical fiber, such as a monofilament 304, as not all embodiments of the present invention are limited in this respect.

In some embodiments, the optical fibers 300 may be made from silica glass and may have wide-angle light dispersion of about 88 degrees. In some embodiments, the optical fibers 300 may be made from plastic fiber with side notches on the fiber. The optical fibers may have diameters between approximately 0.8 mm and approximately 1.7 mm, for example, about 1.5 mm. The optical fibers may be made from any material, such as glass, silicon, silica glass, quartz, sapphire, plastic or any other material, and may have any diameter, as not all embodiments of the present invention are intended to be limited in this respect.

Figure 8:
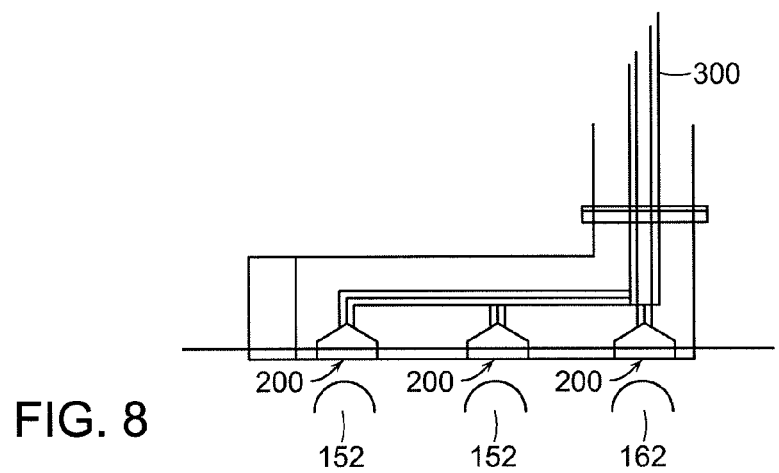
FIG. 8 is a cross-sectional view of an illustrative embodiment of components of a disposable apparatus and optical fibers.
Figure 9:
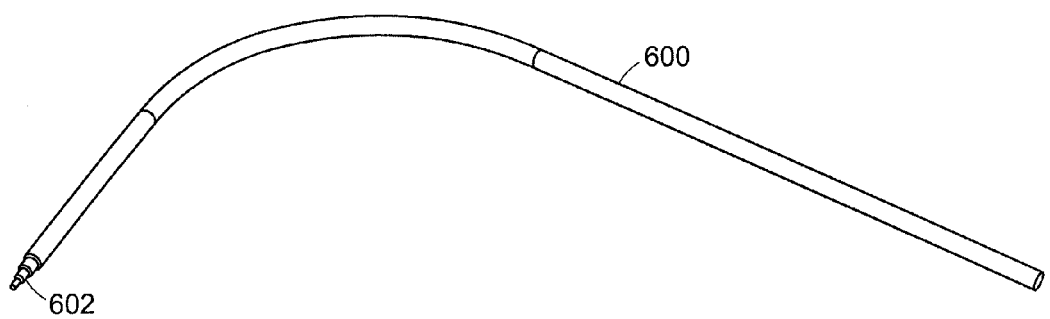
FIG. 9 is a perspective view of an illustrative embodiment of an optical fiber.
Figure 14:
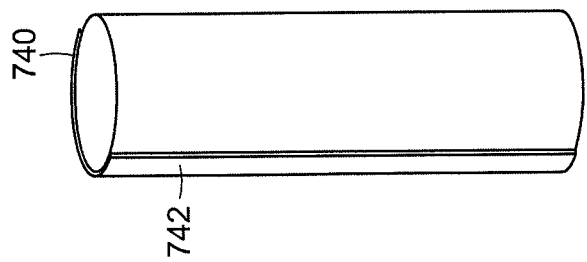
FIG. 14 is perspective view of an illustrative embodiment of a portion of an optical fiber.
Figure 13:
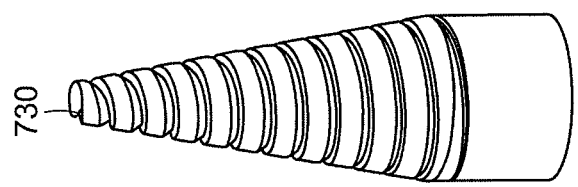
FIG. 13 is perspective view of an illustrative embodiment of a portion of an optical fiber.
Figure 12:
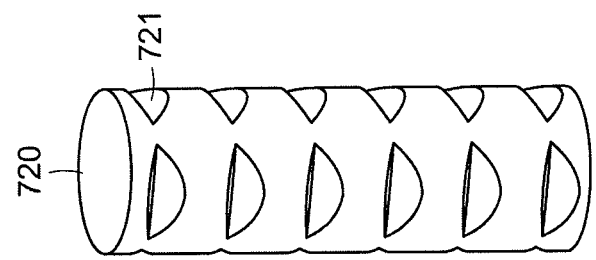
FIG. 12 is perspective view of an illustrative embodiment of a portion of an optical fiber.
Figure 11:
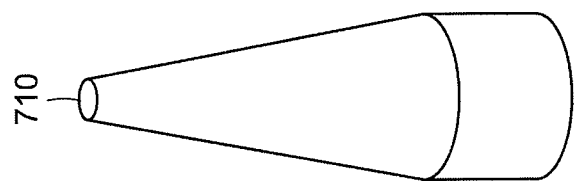
FIG. 11 is perspective view of an illustrative embodiment of a portion of an optical fiber.
Figure 10:
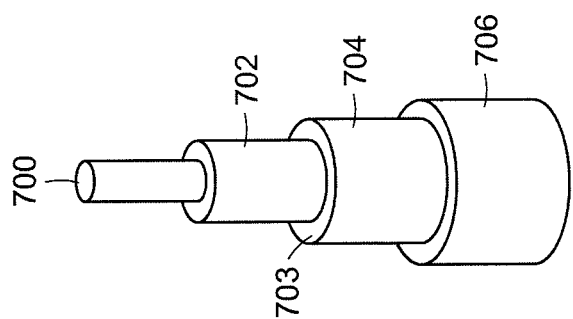
FIG. 10 is perspective view of an illustrative embodiment of a portion of an optical fiber.

FIG. 8 shows a perspective view of an embodiment of an optical fiber 600 for use with a device for repairing a weakened or fractured bone of the presently disclosed embodiments. In some embodiments, an optical fiber similar to the LUMENYTE STA-FLEX SEL end light Optical Fiber, available from Lumenyte International Corporation of Foothill Ranch, Calif., can be employed. These optical fibers may each consist of a light transmitting solid large core, a Teflon® clad and a black bondable outer jacket. The optical fiber 600 may transmit light from a light source to the output end 602 for use as a point source. The optical fiber may have a wide 80 degree acceptance angle and 80 degree beam spread, allowing the light to be viewed from more oblique angles. The light transmitting core may be solid, may have no light diminishing packing fraction losses and may be easily spliced. The jacket may be bondable. Custom jackets may be available for more flexibility and color options.

The optical fiber may each have a transmission loss (attenuation) of less than approximately 1.5% per foot, a bend radius (minimum) of approximately 6 times the fiber's diameter, temperature stability of up to approximately 90° C. (194° F.), spectral transmission range of approximately 350-800 nm, an acceptance angle of approximately 80°, a refractive index core of approximately 1.48 or greater, cladding of approximately 1.34 or less and a numerical aperture of approximately 0.63. The length of the optical fiber may be approximately 100 continuous feet. Splicing may be achieved in the field using a splice kit, such as the Lumenyte Splice Kit, and carefully following the instructions. Factory splicing may be an option. An optic cutter, such as Lumenyte's Optic Cutter, may be advised for straight, clean, 90° fiber cuts. These fibers may be installed by removing approximately 4 inches (10 cm) of the outer jacket (not the fluoropolymer cladding) before inserting fiber into the light source. The fiber end may be near, but not touching the light source glass to assist in achieving maximum brightness. In some embodiments, the optical fiber has some or all of the properties and/or characteristics exhibited by ESKA™ High-performance Plastic Optical Fiber: SK-10 and SK-60 and/or ESKA™ Plastic Fiber Optic & Cable Wiring, manufactured by Mitsubishi Rayon Co., Ltd., which are all available from Mitsubishi International Corporation of New York, N.Y. It should be appreciated that the above-described characteristics and properties of the optical fibers are exemplary and not all embodiments of the present invention are intended to be limited in these respects.

An optical fiber uses a construction of concentric layers for optical and mechanical advantages. The most basic function of a fiber is to guide light, i.e., to keep light concentrated over longer propagation distances—despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding is usually protected with at least a polymer coating. Light is kept in the "core" of the optical fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face. In some embodiments of the present disclosure, at least a portion of a length of an optical fiber is modified, e.g., by removing the cladding, in order to alter the direction, propagation, amount, intensity, angle of incidence, uniformity and/or distribution of light.

In some embodiments, the tip of the optical fiber may be altered and/or the cladding on the outside of the optical fiber may be altered to change the light dispersion. To more evenly distribute light and consistently deliver light along the length of the balloon, egresses may be created along the length of the optical fibers. FIGS. 10-14 show close-up views of various embodiments of modifications to a length of an optical fiber of the presently disclosed embodiments. In the embodiments shown in FIGS. 10-14, the optical fibers are modified in order to alter the direction, propagation, amount, intensity, angle of incidence, uniformity, dispersion and/or distribution of light. As shown in the embodiment depicted in FIG. 10, circular steps (700, 702 and 704) may be created or cut into an optical fiber 700 of the present disclosure to cause the light to disperse along each terminating face 703 of each circular step (702, 704 and 706) of the optical fiber 700. In some embodiments, it may be desirable to remove some, all, or portions of the cladding of the optical fibers of the present disclosure. As shown in the embodiment in FIG. 11, an optical fiber 710 has been tapered along a length, and some of the cladding has been removed. The tapering of the optical fiber 710 can result in a radial dispersion of light from the optical fiber 710. As shown in the embodiment depicted in FIG. 12, notches 721 can be made into an optical fiber 720 to cause the internal reflectance to be directed outwards at an angle from the notch 721 in the fiber 720.

In some embodiments, the notches may be created at about a 45 degree angle to the fiber. In some embodiments, the notches may be created at about a 30 degree angle, about a 62.5 degree angle or any angle less than about 45 degrees or greater than about 45 degrees as not all embodiments of the present invention are intended to be limited in this manner. Further, in some embodiments the angle of the notches may change depending on where the notch is located along the length of the fiber. For example, an optical fiber may be notched so that the angle of the notches which will be positioned at the ends of the balloon have a shallower angle than those to be positioned at middle of the balloon. In some embodiments, the ends of the individual optical fibers that make up an optical fiber bundle may be staggered to enable light to emit from the light source at various locations along the length of the fiber. In some of the above described embodiments, the light need only travel a shorter distance to reach the glue, by allowing the light to travel widthwise or radially within the balloon. As shown in the embodiment depicted in FIG. 13, a length of cladding of an optical fiber 730 has been modified by forming a helical design along a length of the optical fiber 730. As shown in the embodiment depicted in FIG. 14, a portion of cladding 742 has been removed from optical fiber 740.

In some embodiments, optical elements may be oriented in alignment with the notches or openings in the optical fibers to adjust the light output. Such optical elements may include lenses, filters, prisms, splitters, diffusers and/or holographic films. The light source, and more specifically, the optical fibers may have some or all of the properties and features listed in U.S. Pat. No. 6,289,150, which is hereby incorporated by reference in its entirety, as not all embodiments of the present invention are intended to be limited in these respects.

In some embodiments, the optical fiber may include an optical fiber core surrounded by cladding and one or more illuminators. The illuminators may be of uniform size and shape positioned in a predetermined, spaced-apart relation, linearly, along a side of the optical fiber core. The optical fiber core may be received in a track and/or holder and/or reflector comprising a channel constructed with a reflective interior surface centered about the illuminators. The holder and/or reflector may be positioned adjacent to or in contact with the plurality of illuminators. A light source may be connected at one end of the optical fiber conduit in a conventional manner so as to cause a TIR effect. The end of the optical fiber conduit opposite the light source may include a reflective surface for reflecting back towards the light source any light remaining in the optical fiber conduit. For longer spans of optical conduit, the conduit may include a second light source.

The illuminators may include any non-uniformity, constructed into the optical fiber core during or after fabrication, that reflects or refracts light such as, for example bubbles, prisms, lenses or reflective material formed in the core during fabrication or after fabrication. Also, notches made from two cuts in the core to remove a wedge of material or singular cuts made in the core may function as the illuminators. Illuminators, such as notches or cuts may be made by using a mechanical cutter which may be capable of cutting the core uniformly and leaving a smooth, texture-free surface. A cutter suitable for this purpose may cut the core without tearing or burning the material. A cutter may have a circular disk shaped knife having a smooth, tooth-free blade that is freely rotatable about an axle located at the center of the disk. The blade may be angled at 45 degrees relative to the longitudinal axis of the core to cut a 90 degree notch wherein material having a crescent or triangular shape is removed from the core.

The notch may function as an illuminator by maximizing the TIR effect of light within the core. This may be due to the core having a different index of refraction from the ambient air in the notch which may direct the light across the core and out the opposite side of the core. Different lighting effects may be achieved by replacing the ambient air with other gases or compounds. Imperfections in the cut may direct some light into the notch. This light may reflects back through the core.

In some embodiments, where cuts are preferred over notches, the cut may be made at a uniform depth of ⅛ inch into the cladding and core and at a 45 degree angle from the horizontal, i.e., the longitudinal axis of the optical fiber. This may appear to cause the light to exit perpendicular to the longitudinal axis of the optical fiber where the optical fiber core may have an acceptance angle of approximately 81 degrees to allow light to exit. The surface of the sides of the cut may be smooth rather than rough to ensure light is refracted uniformly. The cut may form a wedge which has a gap sufficient to prevent contact between the sides of the cut during normal use. Such contact may reduce the light reflecting and/or refracting properties. In some embodiments, the cuts may be less efficient than the notches in relying on TIR to force light out of core. A holder which may fix the optical fibers in desired alignment may also act as a holder and/or reflector. In some embodiments, when the optical fiber may be round in cross section and may be placed in a nonconforming holder such as a rectilinear "U" channel where an open space is created at the bottom of the "U", cuts may be made in the optical fibers that come in close proximity to the bottom of the "U" to maintain this configuration. In some embodiments where a conforming holder may be used, the cuts may close and alter the configuration such that efficiency of light extraction may be reduced. In some embodiments when using a conforming holder, illuminators may be made with notches sufficient to maintain an open space between the holder and notched surface.

In some embodiments, cutting notches may include using a high speed drill motor with a cutting blade sufficient to make a notch in the optical fiber such that the surface created with the notch may be smooth enough to allow total internal reflection to occur. Alignment of illuminator or illuminators with respect to the holder may determine the directionality of the light output emitted from the optical system. The shape of the cut may effect the output beam pattern of the optical system. For example, the wider the cut, the wider the output beam pattern As with most linear fiber optics, as light is extracted from lengths of the fiber near the light source there may be less light available in subsequent lengths and this occurrence may be taken into consideration in the manufacturing process. In some embodiments, to achieve uniform lighting from the optical fiber conduit, the frequency with which the illuminators occur may increase non-linearly in relation to the length of the conduit and the distance of the illuminators from the light source. In other words, the illuminators may be closer together as the distance from the light source increases. This may compensate for the attenuation of the light due to the loss experienced from the illuminators and the natural attenuation of the optic itself. The spacing may be made progressively closer or in groups of spacing in which the groups may progressively get closer but the distance between individual illuminators within each group may remain constant. In some embodiments, the illuminators may have progressive depths to make the optical fibers transmit light evenly along its length. When illuminators are made progressively deeper, the light pattern may be altered. The deeper the cuts, the wider the light pattern may become. When illuminators are made progressively closer, the light pattern may remain the same and the light output may be increased. In some embodiments, near uniformity of light output along the length of the conduit may be achieved in part due to the changes in the spacing of the illuminators and in part due to the uniformity of the size and angle of the illuminators. A mechanical cutter may be well adapted to provide such uniformity.

While some embodiments may include continuous variations in the frequency of the cut spacing, the cutter may be adaptable to vary the frequency of the spacing at discrete intervals to minimize delays during adjustment of the spacing interval.

The illuminators may be made in optical fiber core alone before the cladding is added and/or the illuminators may be made in the cladding and the core after it has been surrounded by the cladding. In some embodiments, when the cladding is heated to tightly shrink around the core, the cladding may affect the uniformity of the illuminators in the core by either entering the notch or closing the cut thereby reducing the potential light deflecting properties of the illuminator.

The illuminators may be positioned to direct light across the greater diameter of an elliptical optical fiber core out and out through a region opposite from each of the respective illuminators. This may be accomplished by angling the notches and/or cuts to direct light from the light source through the optic core. The illuminators allow better control of escaping light by making the notches, which are positioned on one side of the optic to direct the light rather than allowing the cuts to reflect/refract light in various directions which reduces the contribution of light to a desired focusing effect.

One or more optical elements, such as diffusers, polarizers, magnifying lenses, prisms, holograms or any other element capable of modifying the direction, quantity or quality of the illumination, individually or in combination can also be added and aligned with the core-clad, notches and track or holder and/or reflector. The optical elements may be formed as separate components or formed integrally with the core, cladding and/or a jacketing material or in any combination of separate and integrally formed components. Optical elements formed integrally in the core and cladding of various shapes may create a lens and thereby affects the directionality of light from the finished product. Different optical fiber shapes may create different output beam patterns. In some embodiments, a round fiber optic may create a wider beam spread of light. In some embodiments, a wedge shaped optic may produce a collimated light beam spread. This beam spread may be due to what is believed to be a lensing effect. In some embodiments, the depth of the cut may at least intersect the focal point of the lens formed by the curvature of the optical fiber core where the light exits the core.

The optical fiber core may have any shape and the shape of the core may effect the diffusion of light. In some embodiments, the optical fiber core may be cylindrically shaped when viewed in cross-section and may form a lens that diffuses the light over a wide field of illumination. In some embodiments, the optical fiber core may have an oval or elliptical shape when viewed in cross-section and may form a lens that increases the intensity of the light within a narrower field of illumination. In some embodiments, the optical fiber core may have a wedge shape when viewed in a cross-section and may forms a lens. It will be appreciated that other shapes may be used because of their desired optical characteristics to also act as optical elements, as not all embodiments of the present invention are intended to be limited in this respect.

Alternative optical elements may also assist in achieving various lighting effects by including a separate optical element in alignment with the holder and/or reflector and the arc formed by the notch on the opposite side of the optic from the optical element. The lens optic, notch and holder and/or reflector may be aligned to direct light out of the optic and into the lens. The optical element may also be formed integrally in the jacketing material. The jacket thickness may be adjusted to achieve a desired lighting effect. Alternatively, cylindrically shaped diffusers may be included and aligned to generate other desired lighting effects. In some embodiments, a first diffuser may lower the intensity of light passing through an optical fiber and a second diffuser may increase the intensity of light passing through it. The two diffusers as thus described, may modify the intensity of light as it transmits and diverges away from the optical fiber.

In order to best make use of this kind of application specific optical lighting, it may be advisable to control the alignment of the illuminators, holder and/or reflectors and optical elements. In some embodiments, the alignment of these elements may be centered about a diameter of the fiber optic core (e.g., the diameter from and perpendicular to the center of the holder and/or reflector). It may be desirable to maintain control of this alignment along the entire length of the optical fiber conduit.

The optical fibers 300 may be inserted into a catheter 320 for insertion into a subject's body. In some embodiments, the catheter 320 may have an elongated shaft with a distal end 322, a proximal end 324 and a longitudinal axis therebetween. The distal end 322 of the catheter 320 may have a balloon 330, or another expandable device, that inflates and deflates. In some embodiments, the balloon 330 may be round, flat, cylindrical, oval, rectangular or another shape. In some embodiments, monomer, a polymer or epoxy, such as UV or visible light activated glue, may be used to inflate and deflate the balloon 330. A separation area 332 may be located at the junction between the balloon 330 and the catheter 320. The separation area 332 may also be an illumination band. When activated, the illumination band may cause light to cure glue located in the catheter within the illumination band. The illumination band may include light guides which transmit light of the proper frequency to the illumination band. In some embodiments, light is provided to the light guides by the optical fibers 300; in some embodiments, the light guides are at least part of the optical fibers 300; and in some embodiments, the light guides are separate from the optical fibers 300, as not all embodiments are intended to be limited in this manner.

In some embodiments, it may be desirable for the balloon 330 to separate from the catheter 320, allowing the balloon 330 to remain in the bone 400 and the catheter 330 to be more easily removed. For example, in some embodiments, the catheter 320 may include two fused joints and a pre-stressed notch which facilitate a separation of the balloon 330 from the catheter 320, as is described in U.S. patent application Ser. No. 11/789,907, filed Apr. 26, 2007.

A balloon portion of the catheter 320 may be located and inflated at any location along the length of the catheter 320. The catheter 320 may engage a tubular balloon in such a way as to allow for an open communication channel. The ability to inflate and deflate the balloon ensures that alignment of the plurality of bone fragments for proper healing prior to curing the glue. In some embodiments, inflation of the balloon within the inner lumen of the bone conforms to the shape of the inner bone surface, leading to greater contact area, and provides a custom fit. Those skilled in the art will recognize that a balloon can be formed of a pliable, resilient, conformable, and strong material, including but not limited to urethane, polyethylene terephthalate, nylon elastomer and other similar polymers.

In some embodiments, the balloon may be designed to evenly contact the wall of the cavity in the bone. For example, as depicted in the embodiment of FIG. 1, the pre-defined shape of a balloon 330 may be an elongated cylinder. The balloon 220 has two ends 334, 336 and a surface 338 therebetween. The surface 338 of the balloon 330 may be substantially even and/or smooth and substantially mates with a wall 228 of a cavity 402 in the bone 400. The balloon's surface 338 may not be entirely smooth and may have some small bumps or convexity/concavity along its length. In some embodiments, there are no major protuberances jutting out from the surface 338 of the balloon 330. The balloon may be designed to remain within the cavity of the bone and not protrude through any holes or cracks in the bone. In some embodiments, the balloon's outer surface may be flush with the wall of the cavity and when the balloon is inflated, the balloon's outer surface may contact the wall of the cavity along at least a portion of the balloon's surface area. In some embodiments, when the balloon is inflated, a majority or all of the balloon's outer surface does not contact the wall of the cavity and does not extend through any holes or cracks in the bone.

In some embodiments, the balloon may be contoured to fit inside a cavity in a particularly shaped bone. In some embodiments, the balloon may be shaped to fit entirely within the cavity of the bone and not protrude out of the cavity through any holes or cracks in the wall of the cavity of the bone.

A glue or bone reinforcing mixture may be a natural or synthetic material for strengthening, replacing, or reinforcing of bones or bone tissue. Bone reinforcing mixtures include glues, adhesives, monomers, cements, hard tissue replacement polymers, natural coral, hydroxyapatite, beta-tricalcium phosphate, and various other biomaterials known in the art for strengthening, replacing or reinforcing bones. As inert materials, bone reinforcing mixtures can be incorporated into surrounding tissue or gradually replaced by original tissue. Those skilled in the art will recognize that numerous bone reinforcing mixtures known in the art are within the spirit and scope of the presently disclosed embodiments.

The glue may be a Light Cured Materials (LCMs), which utilize energy provided by ultraviolet (UV) or visible light. Being very energetic, UV light can break chemical bonds, making molecules unusually reactive or ionizing them, in general changing their mutual behavior. In some embodiments, a light emitted by a light source may react with a photoinitiator sensitive to UV light or visible light. Photoinitiators may provide important curing mechanisms for addition polymerization.

Using a UV light, the reinforcing material may reduce or eliminate thermal egress and if there is thermal egress, may reduce the duration thereof. More specifically, there may be little or no chemical composition or mixing of materials. The introduction of light may start the photoinitiator and the glue hardens. Once the light is introduced, the material inside the balloon may harden and the materials inside may be affixed in place. Until the light is introduced, the bone placement may not disturbed or rushed as there may be no hardening of a glue until the light is introduced, the balloon may be inflated or deflated due to the viscosity of the glue. The glue may be infused or removed from the balloon due to the low viscosity of the material. In some embodiments, the viscosity of the reinforcing material may be less than approximately 1000 cP. Not all embodiments are intended to be limited in this respect and some embodiments may include reinforcing materials having a viscosity exactly equal to or greater than 1000 cP.

Different light cured materials use photoinitiators sensitive to different ranges of UV and visible light. For example, visible blue light may be useful to the curing process as it allows materials to be cured between substrates that block UV light but transmit visible light (e.g., plastics). Visible light may increase the cure speed of light cured materials since a greater portion of the electromagnetic spectrum is available as useful energy. Further, visible light may penetrate through light cured materials to a greater depth-enhancing cure depth. The light cured materials may cure in such a way that may be sufficient to hold a bone in the correct orientation. More specifically, the ability to inflate, set, adjust, orient bones, and the resulting union of the bone may be available prior to hardening the glue. Examples of light cured materials include those commercially available from Loctite of Henkel Corporation, located in Rocky Hill, Conn.

In some embodiments, a liquid adhesive such as a cationic epoxy having a cationic photo-initiator may be used. A pre-activated epoxy may exhibit a very low shrink rate. To activate, a UV light in about 245 nm to about 365 nm range may be applied to an epoxy and starts a cure reaction. Once the cure reaction is started, that reaction may continue to completion (e.g., even in the dark).

In some embodiments, the reinforcing material may be a bioabsorbable epoxy so the hardened epoxy may be absorbed into the body over time. In some embodiments, the reinforcing material may be cured by chemical activation or thermal activation. Chemical activation includes but is not limited to water or other liquids. In some embodiments, the reinforcing material may be a drying adhesive which has a polymer dissolved in a solvent such that as the solvent evaporates, the adhesive hardens. In some embodiments, the reinforcing material may be a hot or thermoplastic adhesive such that as the adhesive cools, the adhesive hardens. The reinforcing material may not be limited to the embodiments described herein and may be any material that reinforces the bone. Some materials may require or be enhanced by curing via any means, such as UV or visible light, heat, and/or addition or removal of a chemical or substance, may utilize any outside or internal processes to cure the material, or may not require curing.

In some embodiments, the bone reinforcing mixture may be a light cure adhesive (or UV adhesive). A benefit of ultraviolet (UV) curing is that it may be a cure-on-demand process and that adhesives may be free of solvents and include environmentally friendly resins that cure in seconds upon exposure to long wave UV light or visible light. In some embodiments, the UV adhesive may be a single-component, solvent-free adhesive that may not cure until a UV light engages the adhesive, and when that occurs, the adhesive may cure in seconds to form a complete bond with a shear strength. Visible light may penetrate through the epoxy to a greater depth. Since the visible light penetrates through the epoxy, curing of the material may increase as a greater portion of the electromagnetic spectrum is available as useful energy. In this way, light cured materials may utilize energy provided by ultraviolet light or visible light to start a curing process. Light emitted by a source may react with a photoinitiator sensitive to UV light or to visible light. Visible light may allow materials to be cured between substrates that block UV light but transmits visible light. Using the UV light to cure the reinforcing material may assist in holding broken bones in place, in filling of the balloon, and in viewing under a C arm imaging system.

Those skilled in the art will recognize that some light cured materials may be activated by UV light, visible light, x-rays, gamma rays, microwaves, radio waves, long waves or any light having a wavelength less than about 1 nm, between about 1 nm and about 380 nm, between about 380 nm and about 780 nm, or greater than 780 nm, as not all embodiments are intended to be limited in that respect.

Several epoxies known in the art may be suitable for use as bone reinforcing materials and vary in viscosity, cure times, and hardness (durometer or shore) when fully cured. A durometer of a material indicates the hardness of the material, defined as the material's resistance to permanent indentation. Depending on the amount of resultant support that is necessary for a given bone fracture, a specific durometer UV adhesive may be chosen. Alternately, multiple UV adhesives having varying durometers may be chosen for the repair of a bone fracture and be within the scope and spirit of the presently disclosed embodiments. The durometer of a material may be altered to achieve either greater rigidity or a more malleable result. In some embodiments, the shore or durometer of the epoxies may also be varied in a layer-by-layer approach to achieve a softer more malleable outer layer or a rigid internal structure. The shore or durometer may also be altered to ensure the interface between the glue and the bone is flexible similar to natural shock absorption.

The mechanical properties of the epoxies may dictate using methods/measures that are typical for high-strength and high-impact materials including but not limited to, tensile strength and tensile modulus, tensile strength tests, ultimate modulus, Poisson's ratio, hardness measurements like Vickers and Charpy Impact which measures yield strength and toughness.

In some embodiments, the epoxy may have an elastic modulus of about 0.1 to about 50 GPa, preferably about 1 to about 10 GPa. Cranial-facial bones may have an elastic modulus of about 20 GPa, while plexiglass (PMMA, i.e. bone cement) may have an elastic modulus of about 1 to about 2 GPa. Typical epoxies may have an elastic modulus in the range of about 1 to about 3 GPa, but nano-modified epoxies may have about a 3-5 fold or more increase over the original epoxy with only a few percent loading of carbon nanotubes, clay, mica, and other structures.

In some embodiments, carbon nanotubes (CNTs) may be added to the reinforcing material to increase the strength of the glue. Carbon nanotubes are an allotrope of carbon that take the form of cylindrical carbon molecules and have novel strength properties. Carbon nanotubes may exhibit extraordinary strength. Nanotubes are members of the fullerene structural family, which also includes buckyballs. Whereas buckyballs are spherical in shape, a nanotube is cylindrical with at least one end typically capped with a hemisphere of the buckyball structure. Nanotubes are composed entirely of sp2 bonds, similar to those of graphite. This bonding structure, which is stronger than the sp3 bonds found in diamond, provides the molecules with their unique strength. Nanotubes naturally align themselves into "ropes" held together by Van der Waals forces. Single walled nanotubes or multi-walled nanotubes may be used to strengthen the reinforcing materials.

In some embodiments, the glue may have a hardness of approximately Shore D75, may not fracture, may be capable of being cured with visible light, may be capable of being cured in deep pools or with a greater thickness of glue, and/or may have a viscosity below 800 cp. In some embodiments, the glue may have include photoinitiators, an increased sensitivity to about 450 nm, may have a decreased viscosity, may allow curing in deep pools, and/or may work with the a specific delivered light package.

The remote location to where the light is communicated is located in a patient's body. In some embodiments, the remote location is in a bone of a human. The remote location may be located in any part of a human or animal body and/or may be used in medical, mechanical, electrical, chemical, biological or any other arts as not all embodiments are intended to be limited in this respect.

In some embodiments, the intensity of light may be sufficient enough to reach the distal end of the balloon if the optical fibers in held in close proximity to or contacting/abutting the balloon. By knowing the energy required to cure the glue or polymerize the monomer and calculating the distance from the light source to the most distal aspect of the balloon, the inverse square law may be used to calculate how much energy will dissipate over the distance and therefore whether the light source can be abutted to the balloon or need be placed within the balloon so that it is closer to the glue. Not only is the distance from the light source to the glue reduced by placing the light fiber inside the balloon, but the overall necessary intensity of light may be reduced.

In some embodiments, the light source may be activated by a key. The key may have a chip implanted therein. The chip may define the time, intensity and/or frequency of the illumination device. In this embodiment, the cure time may be predefined or preprogrammed such that the doctor or medical professional need not determine the timing, intensity and/or frequency. In some embodiments, the key may serve to inhibit the light source from being turned on inadvertently or prematurely.

A method of delivering light from a disposable light source to a remote location is disclosed. The method may include positioning the optical fibers 300, which are connected to the disposable apparatus 100 proximate a remote location, communicating light from the light source 140 of the disposable apparatus 100 to the remote location via the optical fibers 300, and discarding the disposable apparatus 100 after a single use. The method may also include emitting light from the disposable apparatus 100; curing a substance, such as a bone reinforcing material, disposed at the remote location with light from the light source 140; curing a bone reinforcing mixture disposed in the cavity 402 of the bone 400 with light from the disposable apparatus 100; introducing a bone reinforcing mixture into the cavity 402 of the bone 400 at the remote site via the catheter 320; expanding an expandable device, such as the balloon 330, in the cavity 402 of the bone 400 with the introduced bone reinforcing mixture wherein the expandable device is attached to the catheter 320; curing the bone reinforcing mixture with light from the disposable apparatus 100; pulsing the light from the disposable apparatus 100; pulsing the light at a rate which is set by a user; pulsing the light at a rate which is preprogrammed; programming the disposable apparatus 100 to emit a predetermined amount of energy; programming the disposable apparatus 100 to emit a predetermined amount of energy at a predetermined rate; having a user program the disposable apparatus 100; preprogramming the programming; and/or inputting at least one variable and programming the disposable apparatus 100 to emit a calculated amount of energy at a calculated rate based on the at least one variable, wherein the at least one variable includes at least one of a volume, a mass, a type and a structure of a bone reinforcing material. Some embodiments may include any or all of the above steps as not all embodiments are intended to be limited in these respects.

To create a more portable device, the disposable apparatus may be sized accordingly. In some embodiments, the dimensions of the disposable apparatus may be about four inches by about four inches by about two inches. In some embodiments, the dimensions of the disposable apparatus may each range from about one to about two to about four to about five to about seven to about ten inches. In some embodiments, the volume of the disposable apparatus is between approximately 10 cubic inches and approximately 20 cubic inches. Not all embodiments are intended to be limited in this respect and in some embodiments, the disposable apparatus may have dimensions that are each less than about one inch and/or greater than about seven inches and/or may have a total volume less than about 10 cubic inches or greater than about 20 cubic inches.

In some embodiments, the optical fiber may have a diameter of about 0.75 mm, about 1 mm, about 1.5 mm, about 2 mm, less than about 0.75 mm or greater than about 2 mm as not all embodiments of the present invention are intended to be limited in this respect. The reflectors may have a diameter of about 0.5 inches to about 2 inches, less than about 0.5 inches or greater than about 2 inches and may have a height of about 0.75 inches to about 2.25 inches, less than about 0.75 inches or greater than about 2.25 inches as not all embodiments of the present invention are intended to be limited in these respects.

Although the figures and description describe some embodiments having shapes for each of the parts, these shapes are intended to be exemplary and not restrictive, as not all embodiments are intended to be limited in this manner. In some embodiments, the parts may have any shape. For example, the optical taper 240 may have a conical, cylindrical, or other non-funnel-like shape.

Although the above description suggests materials for various parts of the disposable apparatus, these materials are intended to be exemplary and not restrictive, as not all embodiments are intended to be limited in this manner. Any materials, such as metals, plastics, silicons, glasses, rubbers, woods, foams, or any other natural or synthetic material, having any color, texture or other properties, may be used to make any of the parts of the disposable apparatus. Further, some parts may be made from one material while other parts may be made from another material or one part may be made from more than one material, as not all embodiments are intended to be limited in these respects.

It should be appreciated that a variety of features employed in related arts, such as light sources, fiber optics, light delivery, indicators, timers, power delivery, electronics and bone repair, may be used in combination with or to modify the above-described features and embodiments.

Various aspects of the invention may include the following: a disposable apparatus for providing light including a light emitter; a power source providing energy to the light emitter; and a link communicating light from the light emitter to a device. The disposable apparatus may be supplied for a single-use. The disposable apparatus may be sterilized. The light emitter may be an LED. The light emitter may emit light having a wavelength between about 400 nanometers and about 470 nanometers. The light may have a wavelength of approximately 450 nanometers. The light may have a wavelength of approximately 460 nanometers. The light may have a wavelength of approximately 470 nanometers.

The disposable apparatus may also include a light director to focus light from the light emitter. The light director may surround at least a portion of the light emitter. The light director may have an inner surface which includes a light reflecting media. The light director may be a ring surrounding at least a portion of the light emitter; the ring may have an inner surface including a light reflecting media. The light director may include an optical taper. The optical taper may have a first end distal to the light emitter and the first end may have a face substantially perpendicular to the emitted light.

The power source may be a portable power source. The portable power source may be at least one battery. The at least one battery may be a non-rechargeable battery. The link may be an optical plug into which an optic fiber of the device may be insertable. The optical plug may have a face substantially perpendicular to the emitted light.

The device may be a catheter. The catheter may include a fiber optic cable. The fiber optic cable may be designed to communicate light to cure a substance. The substance may be a glue. The substance may be a bone reinforcing material located in a cavity in a bone.

The disposable apparatus may also include a second light emitter. The second light emitter may emit a second light and the second light may be communicated to the device by the link. The second light emitter may emit a second light at a different wavelength than the light emitted by the light emitter. The light may have a first wavelength of approximately 365 to 390 nanometers and the second light may have a second wavelength of approximately 436 to 470 nanometers.

The disposable apparatus may also include a switch controlling a flow of energy to the light emitter. The switch may include an on/off switch. The switch may include a timer. The timer may include a pulse function. The pulse function may be set by a user. The disposable apparatus may be preprogrammed to emit a predetermined amount of energy for a predetermined amount of time.

The disposable apparatus may also include a heat sink located proximate the light emitter. The heat sink may be configured to absorb at least a portion of heat from the light source. A volume of the disposable apparatus may be between about 10 cubic inches and about 20 cubic inches.

The device for connecting a fiber to a light source may include a light source oriented to emit light in at least a first direction; a light director surrounding at least a portion of the light source, the light director having a face substantially perpendicular to the first direction; and a connector extending from the light director, the connector being positioned such that when an end of a fiber may be inserted into the connector, the end of the fiber may be correctly aligned with the face of the light director. The light source may be an LED. The light may have a wavelength between about 400 nanometers and about 470 nanometers. The light may have a wavelength of approximately 450 nanometers. The light may have a wavelength of approximately 460 nanometers. The light may have a wavelength of approximately 470 nanometers. The light director may surround at least a majority of the light source. The light director may encircle the light source. The light director may have an inner surface which includes a light reflecting media.

The light director may be a ring surrounding at least a portion of the light source, and the ring may have an inner surface including a light reflecting media. The light director may include an optical taper. The optical taper may have a first end distal to the light source and the first end may have a face substantially perpendicular to the emitted light. The optical taper may have a second end proximate the light source and the second end may have a second face substantially perpendicular to the emitted light. When the end of the fiber is inserted into the connector, the end of the fiber may be adjacent the face of the optical taper.

The device may further include an epoxy located between the end of the fiber and the face of the optical taper. The light director may include a ring surrounding at least a portion of the light source, an optical taper having a second end proximate the light source, and a lens located between the ring and the second end of the optical taper. The connector may include a bracket. The connector may include a locking mechanism to lock the end of the fiber in the connector. The connector may include an alignment ring. The fiber may be an optical fiber.

The device may also include the fiber. The fiber may be an optical fiber. The device may also include a second light source. The second light source may emit a second light into the light director.

The device may also include a second light director surrounding at least a portion of the second light source. The device may also include a second fiber extending from the second light director and the second fiber may communicate light from the second light source to the fiber. The second light source may emit a second light at a different wavelength than the light emitted by the light source. The light may have a first wavelength of approximately 365-390 nanometers and the second light may have a second wavelength of approximately 436-470 nanometers.

The device may also include a third light source. The second light source may emit a second light, the third light source may emit a third light, and the second and third lights may be emitted at different wavelengths than each other and than the light emitted by the light source.

When the end of the fiber is correctly aligned with the face of the light detector, the end of the fiber may be substantially flush with the face of the light detector. When the end of the fiber is correctly aligned with the face of the light detector, a center of the end of the fiber may be aligned with a center of the face of the light detector. When the end of the fiber is correctly aligned with the face of the light detector, an outermost perimeter of the end of the fiber may be aligned with an outermost perimeter of the face of the light detector.

A system for delivering light to remote location includes a light source; an expandable device for insertion into a bone; and a link for communicating light from the light source to the expandable device. The light source may be an LED. The light may have a wavelength between about 400 nanometers and about 470 nanometers. The light may have a wavelength of approximately 450 nanometers. The light may have a wavelength of approximately 460 nanometers. The light may have a wavelength of approximately 470 nanometers.

The light source may also include two light emitters. The two light emitters may be LEDs. The two light emitters may include a first light emitter emitting a first light and a second light emitter emitting a second light and the first light may have a different wavelength than the second light. The light source may include a light director to focus the light. The light director may surround at least a majority of the light source. The light director may encircle the light source. The light director may have an inner surface which includes a light reflecting media. The light director may be a ring surrounding at least a portion of the light source and the ring may have an inner surface including a light reflecting media.

The light director may include an optical taper. The optical taper may have a first end distal to the light source and the first end may have a face substantially perpendicular to the emitted light. The optical taper may have a second end proximate the light source and the second end may have a second face substantially perpendicular to the emitted light.

When the end of the fiber is inserted into the connector, the end of the fiber may be adjacent the face of the optical taper. The system may also include an epoxy located between the end of the fiber and the face of the optical taper. The light director may include a ring surrounding at least a portion of the light source, an optical taper having a second end proximate the light source, and a lens located between the ring and the second end of the optical taper.

The expandable device may include an elongate balloon. The expandable device may be preformed to be contained within a cavity of the bone. The expandable device may be shaped to substantially conform to a wall of a cavity of the bone.

The link includes an optical fiber. The system may also include the fiber. The fiber may be an optical fiber. The link may include a bracket. The link may include a locking mechanism to lock an end of the fiber in the bracket. The link may include an alignment ring. The link may include an optic fiber for communicating light from the light source to the expandable device and an optical plug into which the optic fiber may be insertable. The optical plug may have a face substantially perpendicular to the emitted light.

The link may include a catheter. The link may further include an optical fiber disposed within the catheter.

A method of delivering light from a disposable light source to a remote location may include positioning a link connected to a disposable light source proximate a remote location; communicating light from the disposable light source to the remote location via the link; and discarding the disposable light source after a single use. The link may include an optical fiber. The link may include a bracket. The link may include a fiber. The link may include a locking mechanism to lock an end of the fiber in the bracket. The link may include an alignment ring.

The link may includes an optic fiber for communicating light from the disposable light source to the remote location and an optical plug into which the optic fiber may be insertable. The optical plug may have a face substantially perpendicular to the light from the disposable light source. The link may include a catheter. The link may further include an optical fiber disposed within the catheter.

The single use may include one procedure. The single use may include use on one patient. The single use may include use during only one procedure and/or use on only one patient. The remote location may be located in a patient's body. The remote location may be located in a bone.

The disposable light source may be an LED. The light may have a wavelength between about 400 nanometers and about 470 nanometers. The light may have a wavelength of approximately 450 nanometers. The light may have a wavelength of approximately 460 nanometers. The light may have a wavelength of approximately 470 nanometers.

The disposable light source may include two light emitters. The two light emitters may be LEDs. The two light emitters may include a first light emitter emitting a first light and a second light emitter emitting a second light and the first light may have a different wavelength than the second light.

The method may also include emitting light from the disposable light source. The method may also include curing a substance disposed at the remote location with light from the disposable light source. The method may also include curing a bone reinforcing mixture disposed in a cavity of a bone with light from the disposable light source. The method may also include introducing a bone reinforcing mixture into a cavity of a bone at the remote site via a catheter of the link.

The method may also include expanding an expandable device in the cavity of the bone with the introduced bone reinforcing mixture, the expandable device being attached to the catheter. The method may also include expanding an expandable device in the cavity of the bone with the introduced bone reinforcing mixture and the expandable device is attached to the catheter. The method may also include curing the bone reinforcing mixture with light from the disposable light source. The method may also include pulsing the light from the disposable light source. A rate at which the light pulses may be set by a user. The rate at which the light pulses may be preprogrammed. The method may also include programming the disposable light source to emit a predetermined amount of energy. The method may also include programming the disposable light source to emit a predetermined amount of energy at a predetermined rate. A user may program the disposable light source. The programming may be preprogrammed.

The method may also include inputting at least one variable and programming the disposable light source to emit an calculated amount of energy at a calculated rate based on the at least one variable. The at least one variable may include at least one of a volume, a mass, a type and a structure of a bone reinforcing material.

A system for delivering light to a remote location may include a light source, an expandable device for insertion into a bone, and a fiber for communicating light from the light source to the expandable device. The expandable device may be an elongate balloon and may be preformed to be contained within a cavity of the bone. The expandable device may be shaped to substantially conform to a wall of a cavity of a bone.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of delivering light from a disposable light source to a remote location into a cavity of a fractured bone comprising:
   delivering a bone reinforcing mixture through a catheter and into a balloon positioned in the cavity of the fractured bone at the remote location;
   connecting a fiber having a distal portion to a disposable light source, wherein the light source emits light in a first direction,
   providing a light director having at least one light concentrator surrounding at least a portion of the light source wherein a distal end of the at least one light concentrator is attached to a proximal end of an optical taper, the light director includes a face substantially perpendicular to the first direction, the optical taper having a distal end with a face substantially perpendicular to the emitted light and adjacent an end of the fiber;
   providing a connector extending from the distal end of the optical taper that is positioned such that when the end of the fiber is inserted into an optical plug of the connector, an inner surface of the optical plug is contacted by the end of the fiber, so the fiber is aligned with the face of the optical taper, wherein the at least one light concentrator, the optical taper and the connector, each have substantially the same diameter;
   positioning the distal portion of the fiber through the catheter and within the balloon containing the bone reinforcing mixture;
   delivering light from the disposable light source evenly to the bone reinforcing mixture through a terminating face and along a length of the distal portion of the fiber;
   curing the bone reinforcing mixture in the balloon in the cavity of the fractured bone with light emitted from the disposable light source to the distal portion of the fiber located in the balloon away from walls of the balloon, while the balloon is connected to the catheter; and
   discarding the disposable light source after a single use.

2. The method of claim 1 further comprising pulsing the light from the disposable light source.

3. The method of claim 2 wherein a rate at which the light pulses is either set by a user or preprogrammed.

4. The method of claim 1 further comprising programming the disposable light source to emit a predetermined amount of energy.

5. The method of claim 1 further comprising inputting at least one variable and programming the disposable light source to emit a calculated amount of energy at a calculated rate based on the at least one variable, wherein the at least one variable includes at least one of a volume, a mass, a type and a structure of a bone reinforcing material.

6. The method of claim 1 wherein delivering the bone reinforcing mixture into the balloon engaged with the catheter that inflates and deflates in the cavity of the fractured bone.

7. The method of claim 1 wherein the bone reinforcing mixture is a light cured material.

8. The method of claim 1 wherein the bone reinforcing mixture is a light cure adhesive, and wherein the light source produces visible light.

9. The method of claim 1 wherein at least a portion of a cladding surrounding the distal portion of the fiber is removed to form a helical design in the cladding along a length of the distal portion of the fiber.

10. The method of claim 1 wherein the at least one light concentrator includes a ring that circumvents at least a majority of an outer edge of the light source, and the optical taper surrounds at least a portion of the light source, such that the ring, the optical taper or both have a light reflecting media to direct the light from a larger diameter to a smaller diameter.

11. The method of claim 10 wherein the optical taper includes a second end proximate the light source, the second end having a second face substantially perpendicular to the first direction and substantially parallel to the first face.

12. A method of delivering light from a disposable light source to a remote location inside a cavity of a fractured bone comprising:
    delivering a bone reinforcing mixture through a catheter and into a balloon positioned inside the cavity of the fractured bone at the remote location;
    connecting a fiber having a distal portion to a disposable light source, wherein the light source emits light in a first direction,
    providing a light director having at least one light concentrator surrounding at least a portion of the light source wherein a distal end of the at least one light concentrator is attached to a proximal end of an optical taper, the light director includes a face substantially perpendicular to the first direction, the optical taper having a distal end with a face substantially perpendicular to the emitted light and adjacent an end of the fiber;
    providing a connector extending from the distal end of the optical taper that is positioned such that when the end of the fiber is inserted into an optical plug of the connector, an inner surface of the optical plug is contacted by the end of the fiber, so the fiber is aligned with the face of the optical taper, wherein the at least one light concentrator, the optical taper and the connector, each have substantially the same diameter;
    positioning the distal portion of the fiber through the catheter and within the balloon containing the bone reinforcing mixture;
    delivering light from the disposable light source evenly along a length of the balloon through a terminating face and along a length of the distal portion of the fiber;
    curing the bone reinforcing mixture within the balloon with light emitted from the disposable light source to the distal portion of the fiber located in the balloon away from walls of the balloon, while the balloon is connected to the catheter; and
    discarding the disposable light source after a single use.

13. The method of claim 12 further comprising pulsing the light from the disposable light source.

14. The method of claim 13 wherein a rate at which the light pulses is either set by a user or preprogrammed.

15. The method of claim 12 further comprising programming the disposable light source to emit a predetermined amount of energy.

16. The method of claim 12 further comprising inputting at least one variable and programming the disposable light source to emit a calculated amount of energy at a calculated rate based on the at least one variable, wherein the at least one variable includes at least one of a volume, a mass, a type and a structure of a bone reinforcing material.

17. The method of claim 12 wherein the bone reinforcing mixture is a light cured material.

18. The method of claim 12 wherein the bone reinforcing mixture is a light cure adhesive, and wherein the light source produces visible light.

19. The method of claim 12 wherein positioning the fiber proximate the remote location results in positioning the fiber within the balloon that is engaged with the catheter.

20. The method of claim 12 wherein at least a portion of a cladding surrounding a distal portion of the fiber is modified to form a helical design in the cladding along a length of the distal portion of the fiber.

21. A method of delivering light from a disposable light source to a remote location within a cavity of a fractured bone comprising:
    delivering a bone reinforcing mixture through a catheter and into a balloon positioned within the cavity of the fractured bone at the remote location;
    positioning a distal portion of a fiber through the catheter and within the balloon containing the bone reinforcing mixture, the fiber being connected to a disposable light source, wherein the light source emits light in a first direction,
    providing a light director having at least one light concentrator surrounding at least a portion of the light source wherein a distal end of the at least one light concentrator is attached to a proximal end of an optical taper, the light director includes a face substantially perpendicular to the first direction, the optical taper having a distal end with a face substantially perpendicular to the emitted light and adjacent an end of the fiber;
    providing a connector extending from the distal end of the optical taper that is positioned such that when the end of the fiber is inserted into an optical plug of the connector, an inner surface the optical plug is contacted by the end of the fiber, so the fiber is aligned with the face of the optical taper, wherein the at least one light concentrator, the optical taper and the connector, each have substantially the same diameter;
    delivering light from a disposable light source evenly along a length of the balloon to the bone reinforcing mixture through a terminating face and along a length of the distal portion of the fiber;
    curing the bone reinforcing mixture within the balloon with light emitted from the disposable light source to the distal portion of the fiber located in the balloon away from walls of the balloon, while the balloon is connected to the catheter; and
    discarding the disposable light source after a single use.

22. The method of claim 21 further comprising programming the disposable light source to emit a predetermined amount of energy.

23. The method of claim 21 wherein the bone reinforcing mixture is a light cured material.

24. The method of claim 21 wherein the bone reinforcing mixture is a light cure adhesive, and wherein the light source produces visible light.

25. The method of claim 21 wherein at least a portion of a cladding surrounding a distal portion of the fiber is modified to form a helical design in the cladding along a length of the distal portion of the fiber.

26. The method of claim 21 wherein the connector includes an optical plug having an inner surface in communication with an end of the fibers, wherein the inner surface is located perpendicular to the first direction and parallel and engaging the first face of the light director.

* * * * *